United States Patent [19]
Fitzpatrick et al.

[11] Patent Number: 5,654,178
[45] Date of Patent: Aug. 5, 1997

[54] IMMUNOASSAY FOR TETRACHLOROISOPHTHALONITRILE (CHLOROTHALONIL), ITS DERIVATIVES AND BREAKDOWN PRODUCTS

[75] Inventors: Donna A. Fitzpatrick, Chester Springs, Pa.; Bharat B. Kikani, Marlton; Frank P. Petersen, Burlington Township, both of N.J.; James H. Rittenburg, Perkasie, Pa.

[73] Assignee: ISK Biosciences Corporation, Mentor, Ohio

[21] Appl. No.: 484,687

[22] Filed: Jun. 7, 1995

Related U.S. Application Data

[63] Continuation of Ser. No. 038,438, Mar. 29, 1993, abandoned

[51] Int. Cl.$^6$ .............................. C12N 5/12; C07K 16/44
[52] U.S. Cl. .................. 435/70.21; 435/345; 530/388.9; 530/391.3
[58] Field of Search .................. 435/240.27; 530/388.9, 530/300; 514/304

[56] References Cited

U.S. PATENT DOCUMENTS

| | | | |
|---|---|---|---|
| 4,530,786 | 7/1985 | Dunbar et al. | 260/112 B |
| 4,822,902 | 4/1989 | Carley et al. | 558/14 |
| 5,064,845 | 11/1991 | Hsu et al. | 514/364 |

FOREIGN PATENT DOCUMENTS

| | | |
|---|---|---|
| 89870059 | 4/1989 | European Pat. Off. . |
| 365818 | 9/1989 | European Pat. Off. . |

OTHER PUBLICATIONS

Kelley et al., 1985, J. Agric. Food Chem., 33:962–965, Chlorsulfuron Determination in Soil Extracts by Enzyme Immunoassay.

Wie et al., 1982, J. Agric. Food Chem., 30:949–957, Development of Enzyme–Linked Immunosorbent Assays for Residue Analysis of Diflubenzuron and BAY SIR 8514.

Ercegovich et a., 1981, J. Agric. Food Chem, 29:559–563, Development of a Radioimmunoassay for Parathion.

Newsome, 1985, J. Agric. Food Chem., 33:528–530, An Enzyme–Linked Immunosorbent Assay for Metalaxyl in Foods.

Fleeker, 1986, J. Assoc. Off. Anal. Chem, 70:874–878, Two Enzyme Immunoassays to Screen for 2,4–Dichlorophenoxyacetic Acid in Water.

*Primary Examiner*—Lila Feisee
*Attorney, Agent, or Firm*—Pennie & Edmonds

[57] ABSTRACT

Novel derivatives of chlorothalanil® (tetrachloroisophthalonitrile, TCPN), permit conjugation of the TCPN derivative to a carrier useful as an immunogen to induce antibodies specific for TCPN or a TCPN metabolite, or a screening antigen to detect such antibodies. Polyclonal and monoclonal antibodies specific for TCPN or a TCPN metabolite, as well as hybridoma cells producing such antibodies are disclosed. Also provided are immunoassay methods for detection and quantitation of pesticide chemicals, in particular, the fungicide TCPN or a TCPN metabolite, and kits containing a TCPN derivative screening antigen, an anti-TCPN or anti-TCPN metabolite antibody useful for performing the immunoassays.

19 Claims, 18 Drawing Sheets

TCPN

5-HYDROXY DERIVATIVE

5-AMIDE DERIVATIVE

5-THIO

4-THIO DERIVATIVE

I.R. (KBr)=3320, 2259, 1566, 1410, 1186, 787. M.P.=356-360 C(lit.360-361 C).

BK-489-35
M.P. = 159.3-161.9

1) COCl2
2) H2NCH2CO2H

STEP 1:  +  $\xrightarrow{\text{4-DMAP}}$

SDS-46851       1       2

STEP 2:

STEP 3:

STEP 4:

| IMMUNOGEN HAPTEN | | SCREENING PLATE | | |
|---|---|---|---|---|
| | | CI-O-55 HOCCH₂NCN—[ring Cl,Cl,CN,Cl] | CI-O-157 RCO(CH₂)₃NHCOCH₂CH₂S-S—[ring Cl,Cl,CN,Cl,CN] | COVALINK 5-OH HOOCCH₂CH₂COO—[ring Cl,Cl,CN,Cl,CN] |
| HOCCH₂NCN—[ring CN,Cl,Cl,Cl] | 9/23/91 RABBIT 2269 | 1:1300 | 1:10 | 1:1000 |
| | RABBIT 2272 | 1:1200 | <1:10 | 1:1000 |
| | 10/7/91 RABBIT 2269 | >1:1300 | <1:10 | 1:1000 |
| | RABBIT 2272 | 1:1300 | <1:10 | 1:2000 |
| [ring Cl,Cl,CN,Cl,CN]SCH₂CH₂COOH | 9/23/91 RABBIT 2270 | 1:15 | 1:15 | 1:1000 |
| | RABBIT 2271 | 1:40 | 1:20 | 1:1000 |
| | 10/7/91 RABBIT 2270 | 1:20 | 1:15 | 1:2000 |
| | RABBIT 2271 | 1:30 | 1:10 | 1:1000 |

FIG.8A

| IMMUNOGEN AND BLEED DATE | SCREENING PLATE | | | | | |
|---|---|---|---|---|---|---|
| HOCCH₂CO— (CI with CN, Cl, Cl ring) | CI-O-111 HOCCH₂CO— ring | CI-O-55 HOCCH₂NCN— ring | CI-O-61 HOCCH₂CN— ring | CI-O-157 RCO(CH₂)₃NHCOCH₂CH₂S-S— ring | COVALINK 5-OH HOOCCH₂CH₂COO— ring |
| CI-B-110 SHEEP 1085 6/19/91 | 1:40 | 1:80 | | | | |
| 7/10/91 | | | 1:400 | 1:60 | 1:6000 |
| 7/31/91 | 1:100 | 1:100 | | 1:40 | 1:8000 |
| | | | | 1:100 | |
| CI-K-112 SHEEP 1086 6/19/91 | 1:10 | 1:20 | | | | |
| 7/10/91 | | | 1:10 | 1:30 | 1:750 |
| 7/31/91 | 1:30 | 1:30 | | 1:30 | 1:2000 |
| | | | | 1:100 | |

FIG.9A

| | | | | |
|---|---|---|---|---|
| CN<br>Cl━╱═╲━CN<br>Cl━╲═╱━Cl<br>HOCH₂C<br>‖<br>O | | | | |
| Cl-B-61<br>SHEEP 1107 | 9/11/91<br>10/16/91<br>11/13/91 | <1:100 | <1:100<br>1:30 | <1:100<br>1:100<br><1:100 | 1:30 | 1:300<br>1:1300 |
| Cl-K-64<br>SHEEP 1108 | 9/11/91<br>10/16/91<br>11/13/91 | <1:100 | <1:100<br><1:10 | <1:100<br>1:4000<br>1:4000 | 1:200<br>1:200 | 1:100<br>1:300 |
| CN<br>Cl━╱═╲━Cl<br>Cl━╲═╱━CN<br>Cl | | | | |
| Cl-B-122<br>SHEEP 1116 | 10/16/91<br>11/13/91 | <1:10 | <1:10 | <1:10<br><1:10 | 1:10 | 1:100 |

FIG.9B

IMMUNOASSAY FOR TETRACHLOROISOPHTHALONITRILE (CHLOROTHALONIL), ITS DERIVATIVES AND BREAKDOWN PRODUCTS

This application is a continuation of application Ser. No. 08/038,438, filed on Mar. 29, 1993 now abandoned.

1. INTRODUCTION

The invention relates to immunoassay methods for detection and quantitation of pesticide chemicals, in particular, the fungicide chlorothalonil (tetrachloroisophthalonitrile, TCPN). Also provided are TCPN derivatives useful for preparing immunogenic and assay conjugates and methods for their preparation, polyclonal and monoclonal antibodies specific for TCPN and TCPN derivatives, and hybridoma cells producing such monoclonal antibodies.

2. BACKGROUND OF THE INVENTION

2.1. Pesticides

The use of synthetic pesticides for plant protection has environmental consequences which are a subject of growing public concern. Detection of pesticides remaining in the environment is therefore a matter of increasing importance. Current methods for detecting pesticide residues are extremely time-consuming and costly, since they require highly specialized and expensive apparatus. There is an urgent need in the art to improve existing detection methods making them cheaper, more efficient and more easily manageable. The desired methods should also be useful outside the laboratory under field conditions, such that they can quickly and reliably provide a grower with information on the presence and concentrations of a given pesticide or metabolite in a soil, water or plant sample. In this regard, it is important that the methods differentiate the active pesticide material from its inactive breakdown products allowing quantitative determination of the percentage of active material actually present in the soil.

The registration and use of pesticides throughout the world requires accurate and precise analysis. Parent molecules, key metabolites and chemical breakdown products must be identified and studied in well-designed laboratory and field trials. In response to the need for detecting lower and lower levels of contaminants in crops, water, soil and farm animals, increasingly sophisticated and sensitive methods of analysis are needed. However, a number of serious limitations of classical methods still remain. Some of these limitations would be overcome by the use of immunoassay technology.

2.2. Immunoassays and Detection of Pesticides

While developed primarily for medical and veterinary use, immunoassays have begun to find more applications in the agricultural arena. For example, immunoassays are available for the detection and quantitation of crop diseases, aflatoxins and certain antibiotics. While immunoassays for pesticide detection have been described in the scientific literature (see below), they have only recently become available commercially.

Immunoassays rely on highly specific antibody reagents and relatively simple analytical apparatus to detect and/or quantify a wide variety of target materials. The antibody, rather than the instrument or operating conditions, provides the analytical specificity. Immunoassays can therefore be performed on relatively crude samples. Furthermore, immunoassay methods have been optimized for use in remote, non-laboratory settings, thus allowing their use not only in the specialized laboratory but also in the field.

Tetrachloroisophthalonitrile (TCPN) is an agricultural and horticultural fungicide currently used in many countries. In Northern Europe, it is also used in wood preservatives. The compound is sold under different trade names: Bravo®, Nopcocide®, Daconil 2787®, and Exotherm Termil® (and will be referred to herein as TCPN). Since it is practically insoluble in water, the compound must be dissolved in organic solvents before use. This substance is associated with contact dermatitis, in both the production plant and in the field (Johnsson, M. et al., *Contact Dermatitis* 9:285–288 (1983)). The compound has sensitizing properties in experimental animals (Matsushita, T. et al., *Industrial Health* 19:77–83 (1981); Fujita, Y., *Acta Med. Univ. Kagoshima* 27:17–37 (1985)) and when tested directly on human skin (Johnsson et al., supra; Matsushita et al., supra; Fujita, supra; Bach, B. et al., *Contact Dermatitis* 6:142 (1980)). These allergenic properties indicate that the compound may have immunogenic properties.

Immunologic methods are known for the detection of certain herbicides, including 2,4-dichlorophenoxyacetic acid (Fleeker, J., *J. Assoc. Off. Anal. Chem.* 70:874–878 (1986)), chlorsulfuron (Kelley, M. et al., *J. Agric. Food Chem.* 33:962–965 (1985)), α-haloacetamides (Winzenburger, P. A. et al. (European Patent Publication EP 340198, 1989), and a variety of pesticides, including diflubenzuron (Wie, S. I. et al., *J. Agric. Food Chem.* 30:949–957 (1982)), metalaxyl (Newsome, W. H., *J. Agric. Food Chem.* 33:528–530 (1985)) and parathion (Ercegovich, C. D. et al., *J. Agric. Food Chem.* 29:559–563 (1981)). A method has also been described for the immunologic detection of atrazine (U.S. Pat. No. 4,530,786). Immunological assays for cyanazine, diclofop-methyl, phentachlorphenol, 2,4,5-T and terbutryn are also known.

All of the above immunological methods utilized polyclonal antisera that were obtained from animals (typically rabbits) which had previously been immunized with an appropriate antigen. More recently, monoclonal antibodies (mAbs) specific for atrazine and its derivatives and breakdown products, and use of such mAbs in immunoassays, has been disclosed (Schlaeppi et al., European Patent Publication EP 365818 (1990)).

Because of their low molecular weight, pesticides are generally not immunogenic, making it difficult to use them to elicit specific antibodies. Hence, development of a pesticide immunoassay requires a number of steps, beginning with the design of derivatives of the pesticide which allow conjugation to a higher molecular weight immunogenic "carrier" while maintaining the structural specificity of the pesticide molecule. Furthermore, for screening antibodies during the process of their production, the pesticide must also be prepared in a form which is often different from the form used to immunize animals. Finally, once an antibody preparation is obtained, (either polyclonal or monoclonal, discussed in more detail below), a sufficiently sensitive immunoassay must be developed.

Basic strategies used in modern immunoassays have been described in numerous references (See, for example, Voller, A. et al., eds., *Immunoassays For The 80's*, University Park, 1981; Voller, A., "The Enzyme Linked Immunosorbent Assay (ELISA)", *Diagnostic Horizons* 2:1–7, 1978, Microbiological Associates Quarterly Publication, Walkersville, Md.; Voller, A. et al., *J. Clin. Pathol.* 31:507–520 (1978); Butler, J. E., *Meth. Enzymol.* 73:482–523 (1981); Maggio, E.

(ed.), *Enzyme Immunoassay*, CRC Press, Boca Raton, Fla., 1980). Of the many known approaches, two appear more applicable to pesticide analysis (Winzenburger et al., supra). Essential to each approach is the generation of calibration curves using known amounts of the desired analyte.

The "sandwich immunoassay" approach utilizes at least two antibodies, each of which recognize different epitopes of the analyte, and does not depend on competitive binding. However, the sandwich approach is not generally applicable to pesticide analysis because of the difficulty (if not impossibility) for two antibody molecules to bind a single small pesticide molecule simultaneously.

The "labeled analyte" method, commonly used in radioimmunoassay (RIA) methods, requires that a sample of the antigen (i.e., the pesticide) be detectably labeled, for example, with a radionuclide. For non-radiometric assays, the pesticide may be covalently bound to an enzyme or fluorescent tracer. A known fixed amount of the labeled pesticide is allowed to compete with the free pesticide in the unknown sample for a limited number of antibody binding sites attached to a solid support such as a microplate well. After washing away unbound labeled and unlabeled pesticide, the amount of label remaining bound in the well is inversely proportional to the amount of pesticide originally in the sample. In principle, the labeled analyte can differ somewhat in structure from the measured analyte, as long as the two molecules compete for the same antibody binding site and the measured analyte inhibits the binding of the labeled analyte in the concentration range of interest.

The "labeled antibody" method is commonly used in enzyme immunoassays (EIAs) such as the enzyme-linked immunosorbent assay (ELISA). Here, a protein conjugate of the pesticide (called a "screening antigen") is prepared using a protein that is preferably different from, and non-cross reactive with, the pesticide carrier which had been used to make the anti-pesticide antibody. This conjugate is immobilized on a solid phase support, such as the surface of a microplate well, resulting in a fixed amount of solid phase pesticide per reaction. A known amount of antibody is added along with the test sample. The immobilized pesticide competes with the free pesticide in the unknown sample for a limited number of antibody binding sites. The interaction between antibody and analyte in the fluid phase inhibits the binding of the antibody to the solid phase pesticide. The antibody bound to the solid phase is detected by an enzyme-conjugated second antibody which is specific for the anti-pesticide first antibody (preferably for the constant region of the heavy chain). Many enzyme-linked second antibodies are commercially available for such use. After washing away unbound second antibody, the immobilized second antibody is typically detected by adding a chromogenic substrate for the enzyme, which results in a colored reaction product which is formed in proportion to the amount of second antibody bound. The amount of reaction product is inversely proportional to the amount of analyte in the unknown sample.

A modification of the "labeled antibody" method utilizes the same screening antigen-coated plates. The anti-pesticide antibody is covalently linked to the enzyme, and this conjugate is incubated with sample in the microplate wells. Pesticide in the sample competes with pesticide on the plate to bind the antibody. The plate is washed to remove unbound antibody-enzyme conjugate, and antibody-enzyme conjugate on the plate is detected by addition of a chromogenic substrate.

2.3. Polyclonal Antisera vs. Monoclonal Antibodies

Most existing pesticide immunoassays are based on the use of conventional polyclonal antisera, which are very heterogeneous in composition; serum obtained from a given animal at a given point in time after immunization contains a plurality of different antibodies having varying affinities for the pesticide. These antibodies are also heterogeneous in their fine specificity, reacting with distinct structural determinants, or "epitopes," of the pesticide molecule. Furthermore, the antibodies are of different immunoglobulin isotypes. As a result of all these sources of heterogeneity, polyclonal antisera are often incapable of distinguishing between closely related compounds, such as, for example, atrazine and its principal breakdown product, hydroxyatrazine.

The development of monoclonal antibody (mAb) technology, based on the creation of hybridomas which produce highly homogeneous mAbs (Kohler and Milstein, *Nature* 256:495–97 (1975)), offers the opportunity for improved pesticide immunoassays. This approach is based on the production of hybridoma cells by fusing an antibody-producing B lymphocyte from a previously immunized donor animal with an immortal tumor cell line, typically a myeloma, to yield an immortal hybridoma. Each hybridoma cell line produces a single species of homogeneous immunoglobulin, only one out of the large number of possible antibodies that can be produced by the entire immune system in vivo following immunization. Thus a given hybridoma cell line produces the antibody product of a single B cell clone, hence the term monoclonal.

The advantages of mAbs over polyclonal antisera are numerous: (a) mAbs can be obtained in large quantities and in highly pure form; (b) mAbs retain their characteristic antigen reactivity and do not vary over time; and (c) hybridomas can be cultured (or stored frozen) for years or decades without losing their ability to produce their mAb. Furthermore, mAbs do not suffer from several limitations and disadvantages inherent in antisera, such as: (a) the need to repeatedly draw blood from the immunized animals; (b) the ongoing need for antigenic material for additional immunizations; and (d) the limited lifespan of a donor animal.

Whereas mAbs have become well-established in both research and in medical diagnostics, the uses of mAbs in agriculture has hitherto been limited largely to screening of plant diseases (see, for example, Hsu H. T. et al. (*Amer. Soc. Microbiol. News* 50:91–101 (1984)) and the development of animal vaccines.

3. SUMMARY OF THE INVENTION

The present invention is directed to immunogens, antibodies, including mAbs, and immunoassays useful in the agricultural setting for detection of pesticides, in particular TCPN and its metabolites.

One objective of the present invention is to prepare a useful immunogen for raising anti-TCPN antibodies, by selecting appropriate TCPN derivatives for conjugation to a carrier for use in immunization and screening. Using this or related immunogens, it is a further objective to produce an antibody specific for TCPN or a TCPN metabolite, preferably the acid/amide metabolite designated 46851.

Using hybridoma/mAb technology, the present invention provides for the first time mAbs with high specificity and affinity for TCPN and its derivatives and metabolites.

The antibodies of the present invention allowed the present inventors to devise an immunoassay which rapidly and reliably detects TCPN on the one hand, or its breakdown products. With an assay having this requisite specificity, it is now possible for the first time to easily determine whether a sample, for example soil, water or crop material, is contaminated with TCPN or its derivative or metabolite.

The present invention is thus directed to an antibody, polyclonal or monoclonal, specific for TCPN or a TCPN metabolite. In one embodiment, the antibody is specific for TCPN and does not cross-react with a metabolite of TCPN, such that, under immunoassay conditions, the antibody does not substantially bind to the TCPN metabolite. In another embodiment, the antibody is specific for a TCPN metabolite, preferably 4-hydroxy-TCPN, and does not cross-react with TCPN, such that, under immunoassay conditions, the antibody does not substantially bind to TCPN.

The above antibody is one which is preferably produced by immunizing an animal with a TCPN derivative conjugated to a carrier. The TCPN derivative preferably has a carbon atom, a nitrogen atom a sulfur atom or an oxygen atom attached to the aromatic ring at position 4 or 5, in place of the chlorine atom of TCPN. A preferred TCPN derivative is selected from the group consisting of a 5-hydroxy-TCPN derivative, a 4-hydroxy-TCPN derivative, a 5-amide-TCPN-derivative, a 4-amide-TCPN derivative, a 5-mercapto-TCPN derivative and a 4-mercapto-TCPN derivative.

The present invention is also directed to a hybridoma cell line producing a monoclonal antibody as described above. A preferred hybridoma cell line has the properties of cell line designated 6F9 (ATCC Accession #HB 11395). This cell line has been deposited with American Type Culture Collection (ATCC), International Depository Authority, 12301 Parklawn Drive, Rockville Md. 20852 on Jul. 1, 1993.

The present invention also provides an immunoassay method for detecting the presence of TCPN or a TCPN metabolite in a sample, which comprises:
  (a) contacting the sample with an antibody specific for TCPN or a TCPN metabolite as described above, and;
  (b) measuring the binding of the antibody to a component of the sample.

In one embodiment is provided an immunoassay method for detecting the presence of TCPN in a sample, which comprises:
  (a) contacting the sample with an antibody specific for TCPN and not cross-reactive with a TCPN metabolite, and
  (b) measuring the binding of the antibody to a component of the sample.

In yet another embodiment is provided an immunoassay method for detecting the presence of a TCPN metabolite in a sample, which comprises:
  (a) contacting the sample with an antibody specific for the metabolite and not cross-reactive with TCPN; and
  (b) measuring the binding of the antibody to a component of the sample.

In one embodiment, the above immunoassay method comprises:
  (a) contacting a sample suspected of containing the TCPN or TCPN metabolite with the antibody immobilized on a solid phase support under conditions which allow the antibody to bind to the TCPN or TCPN metabolite;
  (b) contacting a binding partner specific for the TCPN or TCPN metabolite, preferably a second antibody, with any of the bound TCPN or TCPN metabolite under conditions which allow the binding partner to bind to the TCPN or TCPN metabolite; and
  (c) measuring the binding partner bound or unbound to the solid phase support,
thereby detecting or measuring the TCPN or TCPN metabolite.

In the above immunoassays, the antibody may be a polyclonal antibody or a monoclonal antibody.

Also provided is a competitive immunoassay method for detecting the presence of, or measuring the concentration of, TCPN or a TCPN metabolite in a sample, comprising:
  (a) incubating a sample suspected of containing the TCPN or TCPN metabolite with:
    (i) an antibody specific for the TCPN or TCPN metabolite; and
    (ii) a TCPN derivative immobilized to a solid phase support, thereby forming a reaction mixture, under conditions which allow the antibody to bind to the immobilized TCPN derivative, the TCPN in the sample, or the TCPN metabolite in the sample, wherein, the binding of the TCPN or TCPN metabolite in the sample will competitively inhibit the binding of the antibody to the immobilized TCPN derivative;
  (b) removing from the reaction mixture of step (a) any antibody unbound to the solid phase support and any free TCPN or TCPN metabolite from the reaction mixture;
  (c) contacting a binding partner specific for the antibody with the immobilized antibody under conditions which allow the binding partner to bind to the antibody; and
  (d) measuring the binding partner bound to the carrier, wherein the amount of binding partner bound to the solid phase is inversely proportional to the concentration of TCPN or the TCPN metabolite in the sample, thereby detecting or measuring the TCPN or TCPN metabolite.

In the above immunoassay methods, the assay is preferably an enzyme immunoassay. In a preferred embodiment, a competitive immunoassay method for detecting the presence of, or measuring the concentration of, TCPN or a TCPN metabolite in a sample, comprises:
  (a) incubating a sample suspected of containing the TCPN or TCPN metabolite with:
    (i) an antibody-enzyme conjugate wherein the antibody is specific for the TCPN or TCPN metabolite; and
    (ii) a TCPN derivative immobilized to a solid phase support,
thereby forming a reaction mixture, under conditions which allow the antibody to bind to the immobilized TCPN derivative or the TCPN or the TCPN metabolite in the sample, wherein, the binding of the TCPN or the TCPN metabolite to the antibody will competitively inhibit the binding of the antibody to the immobilized TCPN derivative;
  (b) removing from the reaction mixture of step (a) any antibody unbound to the solid phase support and any free TCPN or TCPN metabolite from the reaction mixture;
  (c) contacting a chromogenic substrate for the enzyme with the immobilized antibody-enzyme conjugate under conditions which allow conversion of the substrate into a colored reaction product; and
  (d) detecting or measuring the colored reaction product, wherein the amount of colored reaction product reflects the amount of antibody-enzyme bound to the solid phase support, and is inversely proportional to the concentration of the TCPN or TCPN metabolite in the sample, thereby detecting or measuring the TCPN or TCPN metabolite.

The present invention is also directed to a composition useful for detecting or measuring an antibody specific for TCPN or a TCPN metabolite, comprising a TCPN derivative immobilized on a solid phase support, wherein the TCPN derivative is capable of binding to the antibody. Preferably, the TCPN derivative is covalently linked to a first carrier, preferably a protein or a peptide, which is immobilized on the solid phase support.

In the above composition, the TCPN derivative preferably has a carbon atom, a nitrogen atom a sulfur atom or an oxygen atom attached to the aromatic ring at position 4 or 5 in place of the chlorine atom of TCPN. A preferred TCPN derivative is selected from the group consisting of a 5-hydroxy-TCPN derivative, a 4-hydroxy-TCPN derivative, a 5-amide-TCPN-derivative, a 4-amide-TCPN derivative, a 5-mercapto-TCPN derivative and a 4-mercapto-TCPN derivative.

Also provide is a composition useful for the production of antibodies specific for TCPN or for a TCPN metabolite, comprising a TCPN derivative conjugated to a macromolecular carrier, preferably a protein or peptide. The TCPN derivative has a carbon atom, a nitrogen atom a sulfur atom or an oxygen atom attached to the aromatic ring at position 4 or 5; the TCPN derivative is preferably selected from the group consisting of a 5-hydroxy-TCPN derivative, a 5-amide-TCPN-derivative, a 5-mercapto-TCPN derivative and a 4-mercapto-TCPN derivative.

The present invention also is directed to an immunoassay method for detecting the presence or measuring the amount of an antibody specific for TCPN or specific for a metabolite of TCPN, comprising:

(a) contacting a sample suspected of containing the antibody with a composition, as described above; and (b) detecting the presence or measuring the amount of antibody in the sample which is bound to the solid phase support, thereby detecting the presence or measuring the amount of the antibody specific for TCPN or the TCPN derivative.

In a preferred embodiment, the above method comprises:

(a) contacting a sample suspected of containing the antibodies with a composition as described above;

(b) allowing any antibodies in the sample to bind to the TCPN derivative;

(c) adding a detectably labeled binding partner for the antibodies, preferably an antibody specific for the TCPN-specific or metabolite-specific antibodies, to the bound antibodies and allowing the binding partner to bind to the antibodies; and (d) measuring the amount of bound or unbound labeled binding partner, thereby detecting or measuring the amount of the antibodies.

The above methods are preferably enzyme immunoassays wherein the detectable label is an enzyme.

The present invention also provides a kit for detecting the presence or measuring the concentration of TCPN or a TCPN metabolite in a sample, the kit being compartmentalized to receive in close confinement therein one or more containers, the kit comprising:

(a) a first container containing a TCPN derivative capable of being immobilized on a solid phase support; and (b) a second container containing an antibody, polyclonal or monoclonal, specific for TCPN or a TCPN metabolite.

The kit may optionally also comprise any one or more of the following components:

(c) a third container containing a detectably labeled binding partner for the antibodies;

(d) a fourth container containing an agent capable of reacting with the detectably labeled binding partner to yield a detectable reaction product. The detectable label is preferably selected from the group consisting of an enzyme, a radionuclide, a fluorescent label, a chemiluminescent label and a bioluminescent label.

A preferred monoclonal antibody in the above kit is the 6F9 monoclonal antibody (ATCC #11395).

The present invention is further directed to a method for isolating from a complex mixture a compound capable of binding to an antibody specific for TCPN or an antibody specific for a TCPN metabolite, comprising:

(a) immobilizing an antibody as described above on a solid phase support or carrier;

(b) contacting the complex mixture with the immobilized antibody allowing the compound to bind to the antibody, and washing away any unbound material; and (c) eluting the bound compound, thereby isolating the compound.

Also provided herein is a method for producing a hybridoma cell line that produces a monoclonal antibody that reacts specifically with TCPN or a TCPN metabolite, the method comprising:

(a) immunizing a donor animal with a TCPN derivative conjugated to a carrier;

(b) obtaining B lymphocytes from the immunized donor animal;

(c) fusing the B lymphocytes with cells of a fusion partner cell line to obtain hybrid cells; and (d) selecting hybrid cells which produce the TCPN-specific or TCPN metabolite-specific antibody by:

(i) culturing the hybrid cells;

(ii) screening the medium of the cultures for the presence of an antibody which binds to TCPN or a TCPN metabolite, thereby detecting antibody producing hybrid cells, and (e) growing the selected hybrid cells, thereby producing the hybridoma cell line.

Also provided is method for producing a monoclonal antibody specific for TCPN or a TCPN metabolite, comprising (a) culturing a hybridoma cell line as described above under conditions which permit antibody production and secretion by the cell line; and (b) obtaining the culture medium containing the antibody.

4. DESCRIPTION OF THE FIGURES

FIGS. 1A–1E show the chemical structure of TCPN and TCPN derivatives. FIG. 1A shows the chemical structure of TCPN. FIG. 1B shows the structure of a 5-hydroxy derivative. FIG. 1C shows the structure of a 5-amide derivative. FIG. 1D shows the structure of 5-mercapto-2,4,6-trichloroisophthalonitrile. FIG. 1E shows the structure of a 4-thio (or 4-mercapto) derivative.

FIGS. 8A and 8B show antibody titers of sera from rabbits immunized with various TCPN derivative immunogenic conjugates tested in EIA on various TCPN derivative screening conjugates.

FIGS. 9A and 9B show antibody titers of sera from sheep immunized with various TCPN derivative immunogenic conjugates tested in EIA on various TCPN derivative screening conjugates.

Figure 11A:
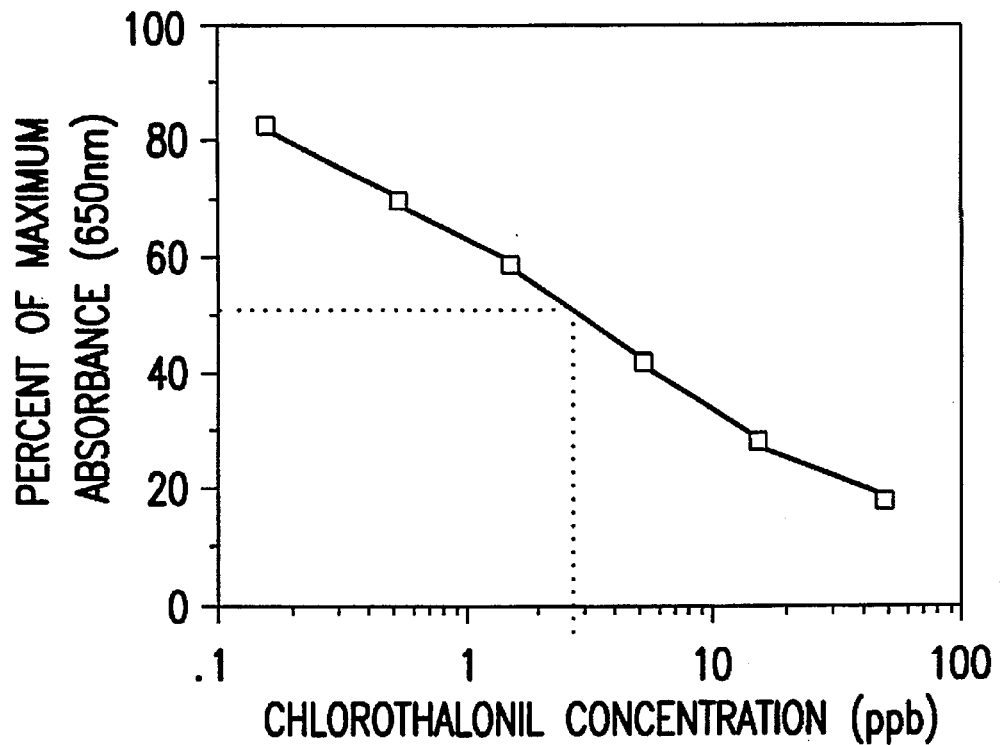
Figure 11B:
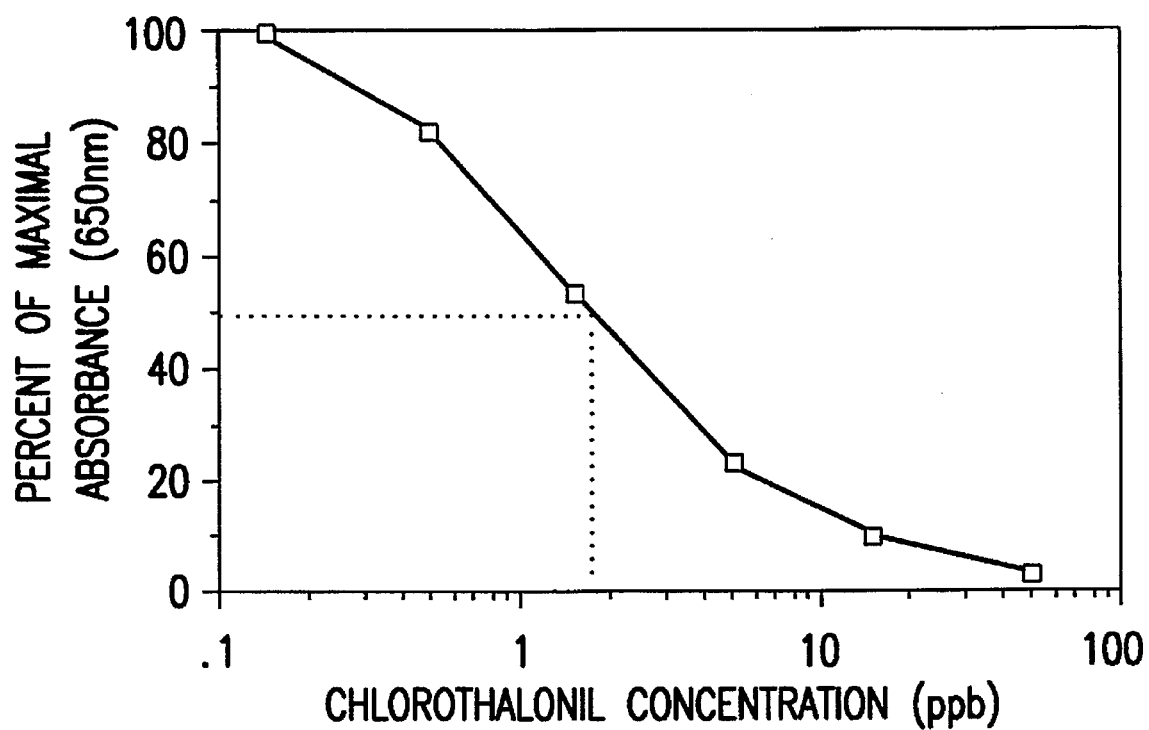

FIGS. 11A and 11B are graphs depicting standard curves of TCPN detection in EIA. FIG. 11A depicts the standard curve of TCPN detection in an EIA using a polyclonal antibody. FIG. 11B depicts the standard curve of TCPN detection in an EIA using mAb 6F9.

Figure 12:
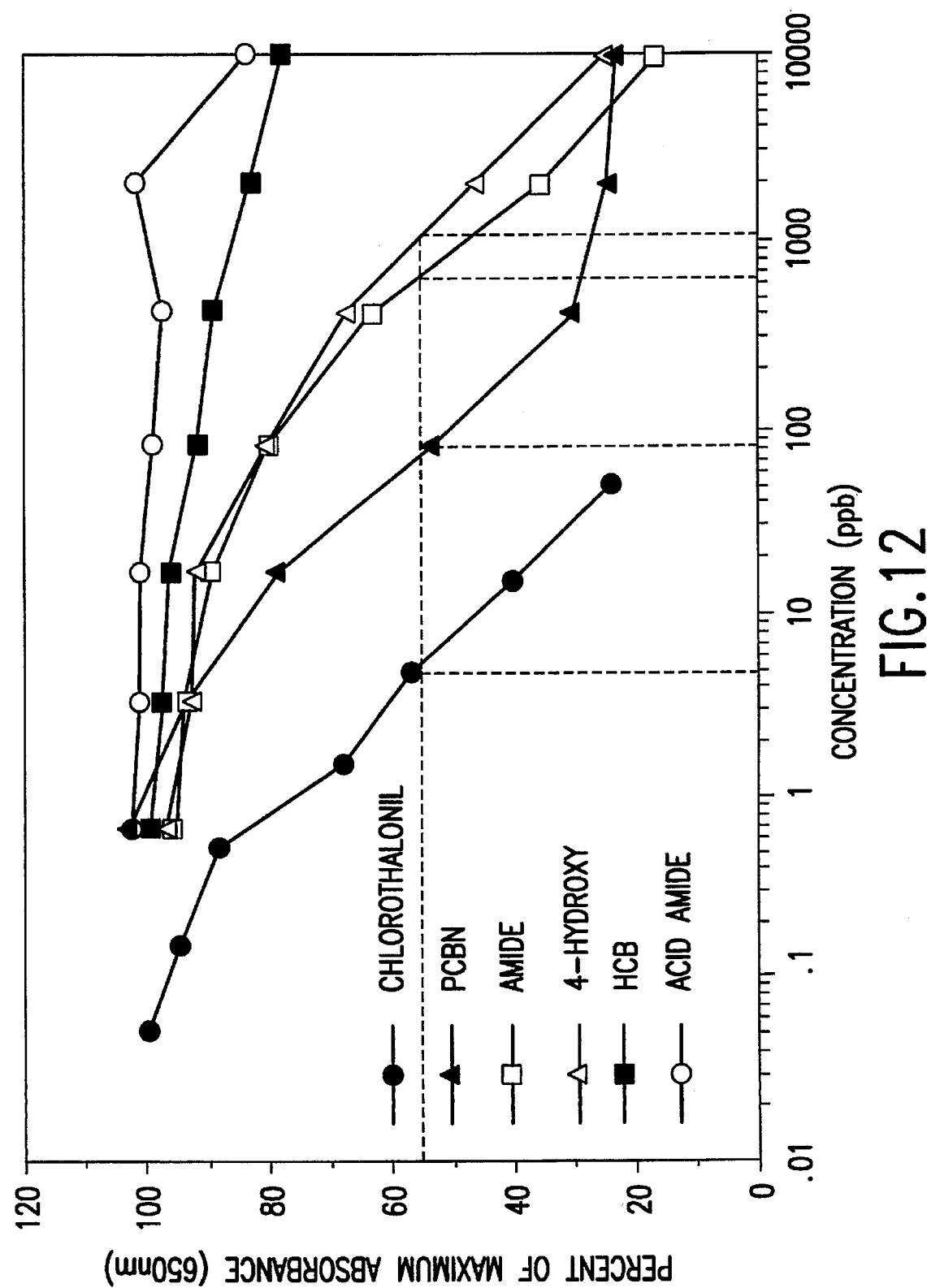

FIG. 12 shows a family of cross-reactivity response curves of TCPN and various derivatives and other organic molecules using the mAb 6F9.

Figure 13:
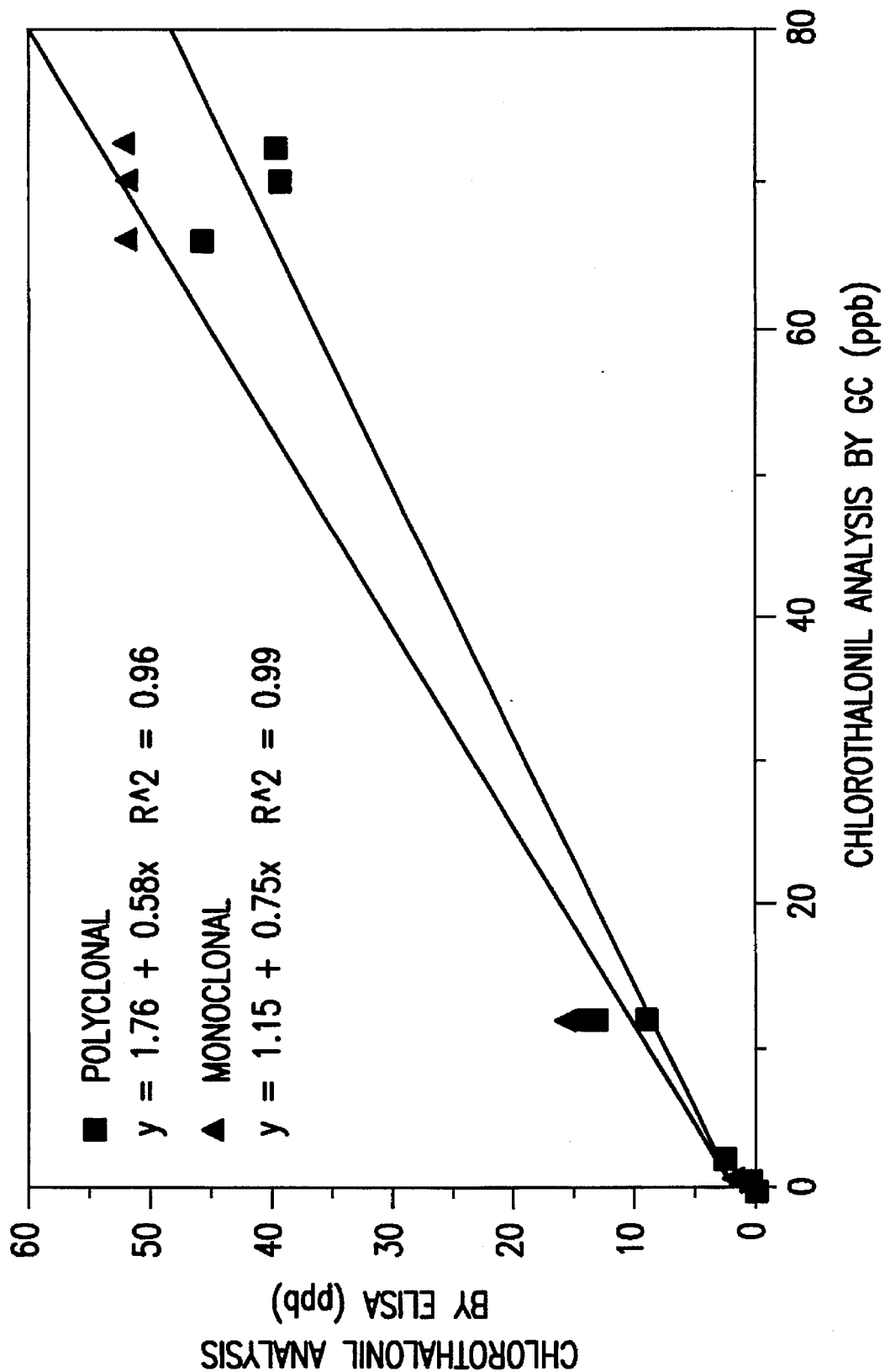

FIG. 13 is a graph showing correlation between the detection of TCPN added to tap water measured by gas chromatography and by EIA using the polyclonal anti-TCPN antibody. The correlation coefficient ($r^2$) is also shown.

Figure 14:
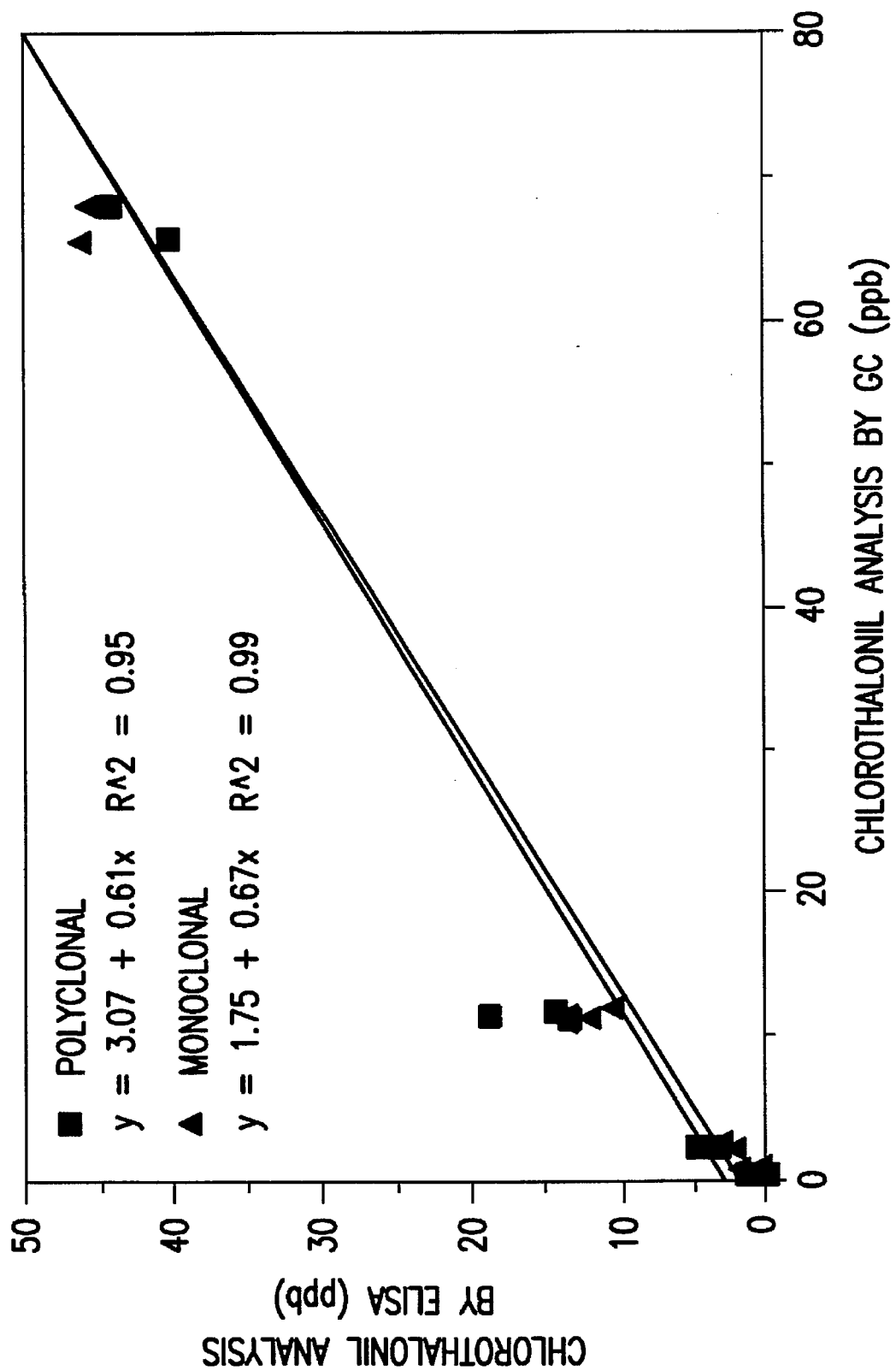

FIG. 14 is a graph showing correlation between the detection of TCPN added to pond water measured by gas chromatography and by EIA using the polyclonal anti-TCPN antibody. The correlation coefficient ($r^2$) is also shown.

Figure 15:
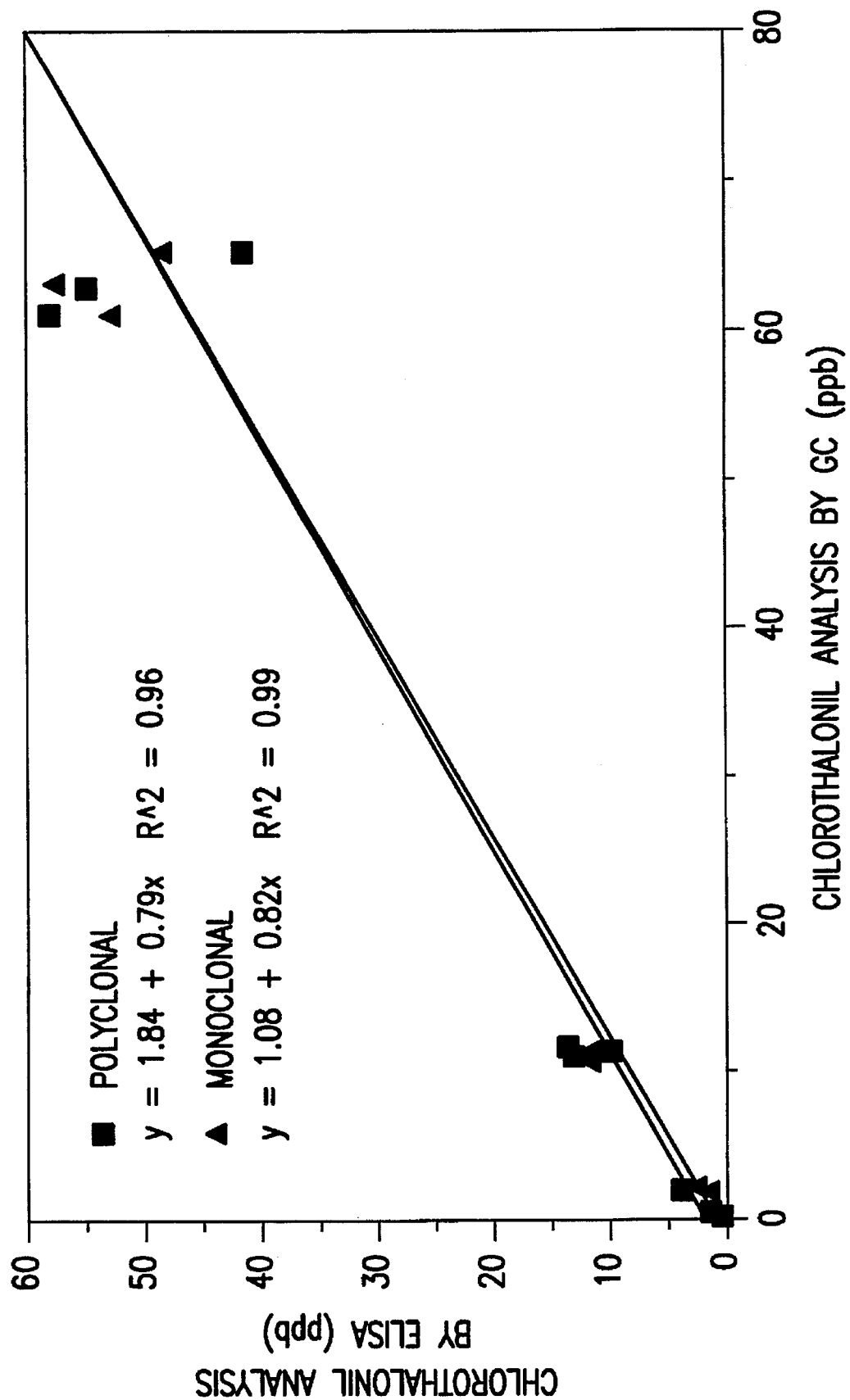

FIG. 15 is a graph showing correlation between the detection of TCPN added to river water measured by gas chromatography and by EIA using the polyclonal anti-TCPN antibody. The correlation coefficient ($r^2$) is also shown.

Figure 16:
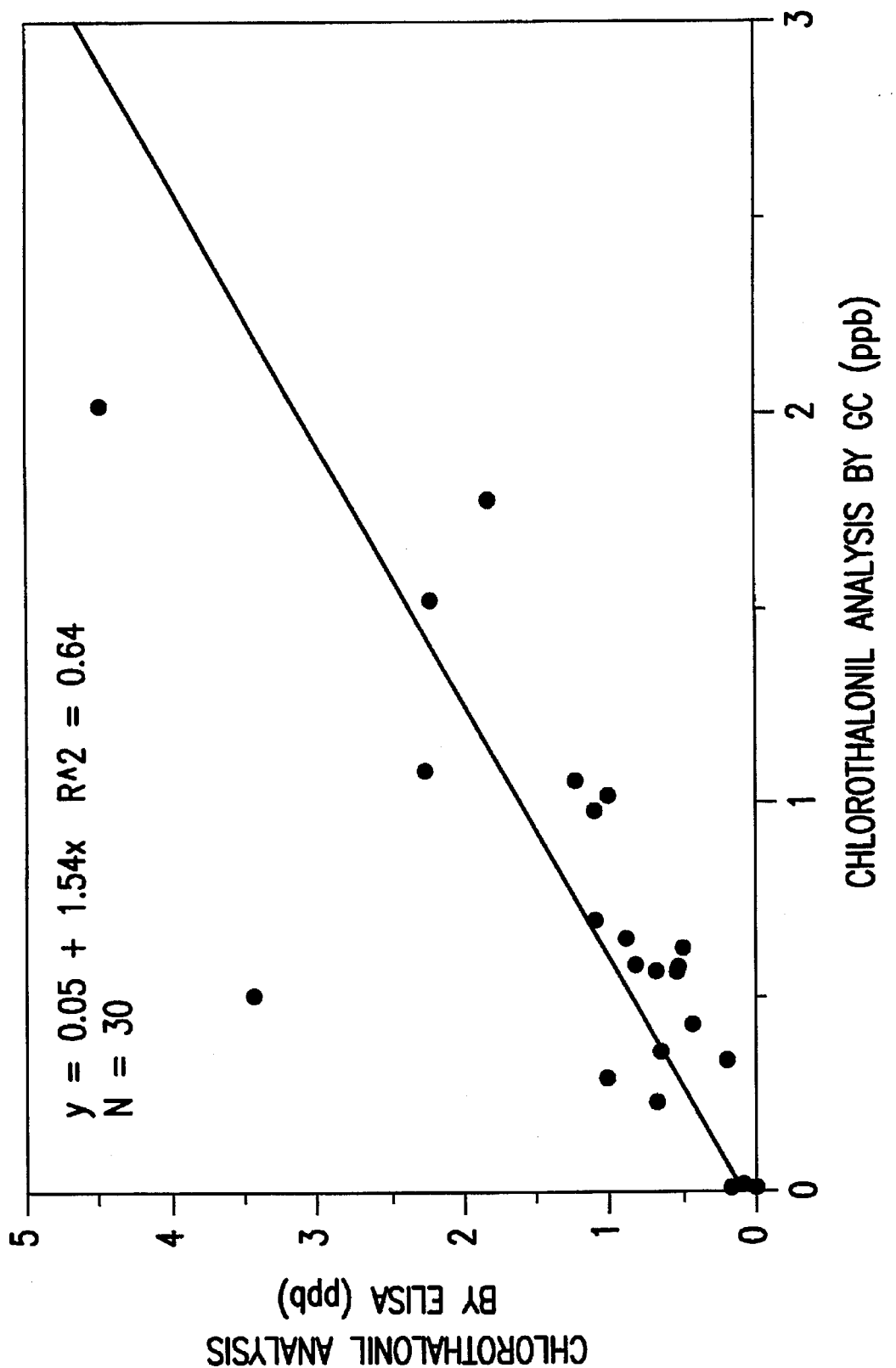

FIG. 16 is a graph showing the correlation between the amount of TCPN detected in a preparation of tomato fruit sprayed with TCPN using gas chromatography vs. immunoassay. The correlation coefficient ($r^2$) is also shown.

5. DETAILED DESCRIPTION OF THE INVENTION

The present inventors have developed methods for producing derivatives of TCPN which can be coupled to relative high molecular weight immunogenic carriers and serve as immunogens for production of TCPN-specific and TCPN metabolite-specific polyclonal and monoclonal antibodies.

The inventors have also created novel hapten (TCPN derivative) molecules and novel hapten-protein conjugates. The TCPN derivatives and conjugates as described herein are useful in screening for, identifying and characterizing anti-TCPN antibodies and in immunoassay methods for detecting TCPN and its metabolites under laboratory and field conditions. Although the present methods are particularly directed to TCPN, they are applicable to any of a number of different pesticides.

As used herein, the term "pesticide" refers to a chemical compound used to control any type of pest (fungal, plant or animal) in an agricultural crop.

Generation of antibodies for immunoassay of small molecules requires attachment of the small molecule, termed a "hapten" to a high molecular weight "carrier," such as a protein. Only in its carrier-bound form is a hapten rendered "immunogenic," that is, capable of stimulating an antibody response following immunization of a host animal. Such attachment or conjugation of a hapten to a carrier is typically accomplished by derivatizing the hapten molecule so that it contains a functional group which can be covalently linked to the carrier, such as a protein, by any of a variety of well known coupling reactions.

TCPN is a relatively small molecule; its structure is shown in FIG. 1. However, substitution of any of its functional groups by a molecular species that would allow conjugation to a protein could potentially result in a modification of TCPN structure sufficient to cause a loss of its antigenic integrity. Thus, in selecting a TCPN analogue or derivative for use in creating a TCPN immunogen (or a TCPN screening antigen), it is important that the TCPN hapten retain the functional groups for which antibody recognition is desired.

A preferred TCPN derivative of the present invention is substituted with a carbon atom, a nitrogen atom, a sulfur atom or an oxygen atom, attached to the aromatic ring at position 4 or 5. Several preferred TCPN derivatives are illustrated in FIG. 1, and include a 5-hydroxy derivative, a 5-amide derivative, a 5-thio derivative and a 4-thio derivative.

The similarity in size and electronic configuration of chlorine (Cl) and sulfur (S) atoms suggested to the present inventors that replacement of one of the Cl atoms of TCPN with an S atom would result in an immunogen that could induce antibodies specific for unmodified TCPN. According to this reasoning, antibodies induced by a 4-mercapto derivative might be predicted to recognize unmodified TCPN more readily than the 4-hydroxy derivative of TCPN. Furthermore, the mode of action of TCPN as a pesticide is believed to involve its binding to sulfur-containing (thiolated) proteins through displacement of the 4-chloro group. In fact, this reaction occurs so readily that, in exposed humans, TCPN binds to autologous proteins and stimulates an allergic reaction, leading to an IgE antibody response.

Thus, the present inventors conceived that an immunogen useful for inducing anti-TCPN antibodies could be prepared by reacting TCPN with a thiolated protein. Thus, in a preferred embodiment of the present invention, a conjugate between TCPN and a protein such as bovine serum albumin (BSA) is prepared by first thiolating the protein with 2-iminothiolane (Traut's reagent) and then adding the TCPN. The resulting conjugate is then used either as an immunogen, to immunize an animal, or as a screening antigen to test an antibody preparation. A conjugate produced in this way by the present inventors was designated Cl-B-122. Specificity of the antibodies for TCPN is readily tested by using unmodified TCPN to inhibit binding of antibodies to the TCPN conjugate.

The approach described above has a wider application than in the conjugation of TCPN to produce an immunogenic form of the molecule. For example, any of a number of agricultural chemicals having a chlorinated benzene ring are susceptible to conjugation by the methods described herein to render them immunogenic, and thus useful for inducing specific antibodies. Non-limiting examples of such chemicals include pentachloronitrobenzene (Quintozene®, Terrachlor®), dichloronitroaniline [DCNA] (Botron®), tetrachlorodimethylacetobenzene; paraminobenzoic acid methyl ester tetrachloride (Dacthal®), 2,4-D and pentachlorphenol.

The TCPN (or other pesticide) derivative of the present invention may be conjugated to any of a number of carrier molecules, preferably proteins. Preferred proteins disclosed herein, and commonly used in immunology, include, but are not limited to, bovine serum albumin (BSA), chicken albumin, keyhole limpet hemocyanin (KLH) and the like. For a discussion of hapten protein conjugates, see, for example, Hartlow, E. et al., *Antibodies: A Laboratory Manual*, Cold Spring Harbor Laboratory Press, Cold Spring Harbor, N.Y., 1988) or a standard immunology textbook such as Roitt, I. et al., *IMMUNOLOGY*, C. V. Mosby Co., St. Louis, Mo. (1985) or Klein, J., *IMMUNOLOGY*, Blackwell Scientific Publications, Inc., Cambridge, Mass., (1990).

In other embodiments of the present invention, any of a number of different paths to achieve coupling through the 4-mercapto position may be used. N-succinimidyl 3-(2-pyridyldithio)propionate (SPDP) can be used to attach the hapten, through a dithio bond and a three carbon spacer, to the ε-amino groups of lysine in a protein. A long chain SPDP analogue, succinimidyl-6-[3-(2-pyridyldithio) propionamido] hexanoate (LC-SPDP), and an aromatic analogue, 4-succinimidyloxycarbonyl-α-methyl-α-(2-pyridyldithio)toluene (SMPT), can be used to prepare conjugates with different bridge structures in an effort to increase stability in vivo and provide conjugates with unique immunogenic properties. For example, a thiopropionic acid derivative at the 4-position of TCPN can be prepared for coupling to a protein through the carboxylic acid functionality.

In other embodiments of the present invention, it may be desirable that functional groups for coupling to the protein (or other carrier) be at a carbon other than the 4-position. Since the 6-position is equivalent to the 4-position, and the 1- and 3-positions are already filled with cyano groups which should preferably be retained for proper steric specificity, the 2- and 5-positions are possible sites for coupling. Steric, electronic, and synthetic considerations make the 5-position a preferred site of attachment.

In one embodiment, a mercapto derivative at the 5-position may be produced. A preferred synthetic approach uses Nickel (II) chloride to decompose the diazonium salt made from 5-amino-TCPN at 10° C., resulting in a faster formation of the xanthate. The xanthate ester was hydrolyzed using acid catalysis instead of KOH, yielding essentially pure 5-mercapto-TCPN (see FIG. 2).

When such a derivative was produced, no amide or carboxylic acid carbonyl absorption (indicating hydrolysis of one or both the cyano groups) was detected by IR spectroscopy; NMR analysis confirmed the identity of the product. This 5-mercapto derivative was used to prepare immunogen and screening conjugates.

In another embodiment, a hydroxy or an amino derivative may be introduced at the 5-position of TCPN. Spacer groups with carboxylic acid functions may be attached at this position, and the resulting haptens coupled to lysine residues of a carrier protein using a mixed anhydride reaction to give an amide bond.

Several immunogens with various functional groups at position 5 have been prepared and antibodies specific for them were produced. While antibodies generated against such immunogens had high titers, they reacted with TCPN at a lower sensitivity than antibodies raised against the Cl-B-122 derivative (described above). Based on these observations, the present inventors concluded that substitution of a chloro group with an oxygen or nitrogen functional group at position 5 results in derivatives which are antigenically more distinct from TCPN than is the Cl-B-122 conjugate.

Given the teachings contained herein, one of ordinary skill in the art will readily appreciate how to prepare conjugates of proteins, or other non-proteinaceous immunogenic carriers, with TCPN or other chlorinated benzene compounds for use as immunogens or screening antigens.

5.1. Production of Antibodies

The immunogenic conjugates of the present invention are used to produce antibodies. Immunization of animals, preferably mammals, most preferably sheep, goats, cows or horses, may be performed by one or more injections on one or more occasions, for purposes of obtaining immune sera (polyclonal antibodies). In a preferred embodiment, an animals, preferably a rodent, most preferably a mouse or rat is immunized on one or more occasions, and the lymphocytes obtained therefrom are fused to myeloma cells to produce a hybridoma.

Hybridomas secreting mAbs specific for TCPN or a derivative thereof are produced by conventional methods. However, it is preferred that after cell fusion using polyethylene glycol, the cells are cultured in HAT medium (RPMI-1640 medium containing standard concentrations of hypoxanthine, aminopterin, and thymidine, with 20% fetal calf serum) supplemented with transferrin at a concentration of about 1 μg/ml. The HT medium (lacking aminopterin), to which cells are subsequently transferred after about 6–7 days, preferably also contains transferrin at about 1 μg/ml.

Immunization regimens are well-known in the art. The immunogen may be injected by any of a number of routes, including subcutaneous (s.c.), intravenous (i.v.), intraperitoneal (i.p.), intradermal, intramuscular, or a combination of these. The immunogen may be injected in soluble form, aggregate form, attached to a physical carrier, or mixed with an adjuvant, using methods and materials well-known in the art.

For production of anti-TCPN mAbs, a preferred schedule for immunizing mice with an immunogenic TCPN conjugate is:

Day 0: 50–150 μg priming immunization, i.p.

Day 14: 50–150 μg booster immunization, i.p.

Day 28: 50–150 μg booster immunization, i.v., and

Day 32: harvest cells for fusion.

The term "antibody" as used herein is meant to include polyclonal antibodies, monoclonal antibodies (mAbs), and anti-idiotypic (anti-Id) antibodies, either polyclonal or monoclonal. As described in the Background section, polyclonal antibodies are heterogeneous populations of antibody molecules derived from the sera of animals immunized with an antigen. Monoclonal antibodies, which are substantially homogeneous population of antibodies, may be obtained by methods known to those skilled in the art. See, for example Kohler and Milstein, supra; U.S. Pat. No. 4,376,110; Hartlow, E. et al., *Antibodies: A Laboratory Manual*, Cold Spring Harbor Laboratory Press, Cold Spring Harbor, N.Y., 1988).

Such antibodies may be of any immunoglobulin class including IgG, IgM, IgE, IgA and any subclass thereof. The hybridoma producing the mAbs of this invention may be cultivated in vitro or in vivo. For production of high titers of mAbs in vivo, cells from the individual hybridomas are injected intraperitoneally into pristane-primed BALB/c mice to produce ascites fluid containing high concentrations of the desired mAbs. MAbs may be purified from such ascites fluids, or from culture supernatants, using column chromatography methods well known to those of skill in the art.

An anti-idiotypic (anti-Id) antibody is an antibody which recognizes unique determinants generally associated with the antigen-binding site of an antibody. Certain anti-Id antibodies resembles an epitope of an antigen to which the original antibody is specific and can thereby be used in place of the antigen (i.e., the pesticide). In one embodiment, an anti-TCPN mAb according to the present invention is produced and used to immunize an animal of the same species and genetic type (e.g., mouse strain) as the source of the mAb. The immunized animal will recognize and respond to the idiotypic determinants of the immunizing antibody by producing an antibody to these idiotypic determinants (the anti-Id antibody). Some of the anti-Id antibodies so produced will cross-react with TCPN or compete with binding of the anti-TCPN antibody with TCPN. Because of the epitopic similarity of some of the above anti-Id antibodies to TCPN (or a derivative thereof), the anti-Id can be used as a surrogate immunogen, in lieu of a TCPN-carrier conjugate, to generate antibodies specific for TCPN or its metabolites. Thus, for example, an anti-Id mAb can be coupled to a carrier such as keyhole limpet hemocyanin (KLH) and used to immunize additional BALB/c mice. Sera from these mice will contain anti-anti-Id antibodies that have the binding properties of the original mAb specific for TCPN and spleen cells of such animals may be used for production of mAbs as described herein.

As used herein, the term "antibody" is also meant to include both intact molecules as well as antigen-binding fragments thereof, such as, for example, Fab and F(ab')$_2$, and Fv. It will be appreciated that such antibody fragments useful in the present invention may be used for the detection and quantitation of TCPN or its metabolites according to the methods disclosed herein for intact antibody molecules. Such fragments are typically produced by proteolytic cleavage, using enzymes such as papain (to produce Fab fragments) or pepsin (to produce F(ab')$_2$ fragments).

5.2. Immunoassays

An immunoassays for detection of TCPN typically comprises incubating a sample suspected of containing TCPN in the presence of an antibody according to the present invention, and detecting the binding of the antibody to the TCPN.

In a direct enzyme immunoassay (EIA, see below), the anti-TCPN antibody is bound to a solid support, preferably the surface of a microplate well. The sample suspected of containing TCPN or a metabolite thereof is mixed with a TCPN-enzyme conjugate and incubated with the antibody-coated solid phase. The amount of enzyme bound to the solid phase is inversely proportional to the amount of TCPN or metabolite in the sample.

In one embodiment of a competitive immunoassay, a known amount of TCPN or a derivative thereof, preferably conjugated to a protein or other carrier, is bound to a solid phase support or matrix. This immobilized TCPN or TCPN derivative is incubated with a detectably labeled anti-TCPN antibody according to the present invention and a test sample suspected of containing TCPN or TCPN metabolite, or a material immunologically cross-reactive therewith. The TCPN or TCPN metabolite (or a cross-reactive component) in the sample competes with the immobilized TCPN for binding to a fixed amount of antibody. The solid phase support may then be washed with a buffer to remove unbound antibody. The amount of bound antibody on the solid support may then be detected by any appropriate means depending on the nature of the detectable label. The amount of bound label is inversely proportional to the amount of TCPN (or cross-reactive component) in the sample.

By "solid phase support" or "solid phase matrix" or "solid phase carrier" is intended any support capable of binding the antigen, or, in other embodiments, of binding an antibody. Well-known supports include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled antigen is capable of binding to an antibody, or a coupled antibody is capable of binding to an antigen. Thus, the support configuration may be spherical, as in a bead, or cylindrical, as in the inside surface of a test tube, or the external surface of a rod. Alternatively, the surface may be flat such as a sheet, test strip, etc. Those skilled in the art will know many other suitable carriers for binding antibody or antigen, or will be able to ascertain the same by use of routine experimentation.

The binding activity of a given lot of anti-TCPN antibody may be determined according to well-known methods using antibody screening antigen preparations prepared as disclosed herein. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which a TCPN-specific (or TCPN derivative-specific or TCPN metabolite-specific) antibody can be detectably labeled is by linking to an enzyme and use in an EIA, such as an ELISA (See, for example: Voller, A., "THE ENZYME LINKED IMMUNOSORBENT ASSAY (ELISA)", *Diagnostic Horizons* 2:1–7, 1978)) (Microbiological Associates Quarterly Publication, Walkersville, Md.); Voller, A. et al., *Bull. WHO* 53:55–65 (1976); Voller, A. et al., *J. Clin. Pathol.* 31:507–520 (1978); Butler, J. E., *Meth. Enzymol.* 73:482–523 (1981); Maggio, E. (ed.), *ENZYME IMMUNOASSAY,* CRC Press, Boca Raton, Fla., 1980; Ishikawa, E. et al. (eds.), *ENZYME IMMUNOASSAY,* Kgaku Shoin, Tokyo, 1981). The enzyme, in turn, when later exposed to its substrate, will react with the substrate in such a manner as to produce a chemical moiety which can be detected, for example, by spectrophotometric, fluorometric or visual means.

Enzymes which can be used to detectably label the antibody of the present invention include, but are not limited to, horseradish peroxidase, alkaline phosphatase malate dehydrogenase, staphylococcal nuclease, Δ-V-steroid isomerase, yeast alcohol dehydrogenase, α-glycerophosphate dehydrogenase, triose phosphate isomerase, asparaginase, glucose oxidase, β-galactosidase, ribonuclease, urease, catalase, glucose-6-phosphate dehydrogenase, glucoamylase and acetylcholinesterase.

The immunoassay may be an RIA, wherein the antibody or fragment is labeled with a radionuclide (see, for example, Weintraub, B., *PRINCIPLES OF RADIOIMMUNOASSAYS,* Seventh Training Course on Radioligand Assay Techniques, The Endocrine Society, March, 1986. The radionuclide can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentaacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Another useful approach for pesticide immunoassays, called Enzyme Multiplied Immuno Technique (EMIT), is a modification of the labeled analyte approach. The analyte is covalently conjugated to an enzyme label close to the active site of the enzyme so that binding of the antibody spatially inhibits the enzyme reaction. When this hapten-enzyme conjugate is incubated with the test sample and the antibody in a homogeneous solution, no physical separation of the bound and unbound moieties is required because only those conjugates which are unbound can be detected when the substrate is added. Therefore, only samples which contain the pesticide will develop a detectable reaction product since the presence of the free pesticide is required to prevent the inhibitory binding of the antibody to the enzyme-hapten conjugate.

5.3. Kits

The present invention also includes means for the qualitative and quantitative determination of TCPN and/or TCPN derivatives and of metabolites of TCPN or of TCPN derivatives in the form of ready-to-use test kits which contain at least one antibody according to the present invention as a reagent. The kit of the present invention is suitable for use under field conditions for the rapid and reliable detection of TCPN and/or TCPN derivatives and of metabolites of TCPN or of TCPN derivatives.

A test kit, in addition to the anti-pesticide (or anti-pesticide derivative) antibodies according to the invention, may optionally contain still other binding partners for these antibodies. The binding partners are preferably detectably labeled, and may be monoclonal or polyclonal antibodies specific for an immunoglobulin isotype of the anti-pesticide antibody.

Particularly preferred within the scope of this invention are test kits which are based on one of the commonly used immunoassays, including EIA, RIA and chemiluminescence assay. More particularly preferred are test kits in which the determination of TCPN or its metabolites is based on a competitive immunoassay, most preferably a competitive EIA.

Test kits for the immunologic detection of TCPN or a TCPN metabolite or derivative, based on an EIA may, for example, contain the following components:

(a) a first container containing a TCPN derivative capable of being immobilized on a solid phase support or, alternatively, immobilized on a solid phase support, preferably a microplate well; and (b) a second container containing an antibody specific for TCPN or for a TCPN metabolite.

(c) optionally, a third container containing a detectably labeled binding partner for the above antibodies. The detectable label is preferably an enzyme. For other assay formats within the scope of this invention, the label may be a radionuclide, a fluorescent label, a chemiluminescent label or a bioluminescent label.

(d) optionally, a fourth container containing an agent capable of reacting with the detectably labeled binding partner to yield a detectable reaction product; use in an EIA, a preferred agent is a chromogenic substrate;

(e) optionally, the TCPN or TCPN derivative or metabolite antigen or standardized solutions of the antigen;

(f) optionally, buffer solutions;

(g) optionally, polypeptides, detergents and additional additives which, for example, prevent nonspecific adsorption and aggregate formation, and (h) optionally, pipettes, reaction vessels, calibration curves, color charts, package inserts, instructions etc.

Commonly used in the manufacture of test kits, for example, are microtiter plates of transparent plastic materials such as, for example, polyvinyl chloride or polystyrene, which may be uncoated or else coated with a screening antigen, or an antibody, according to the invention, with free antibody, or free antigen. Likewise used are small balls, tubes or rods of polystyrene and polystyrene latex, where the surrounding latex material may be separated from the polystyrene particles by centrifugation.

Having now generally described the invention, the same will be more readily understood through reference to the following examples which are provided by way of illustration, and are not intended to be limiting of the present invention, unless specified.

6. EXAMPLE: GENERAL APPROACHES TO HAPTEN SYNTHESIS

Figure 1A:
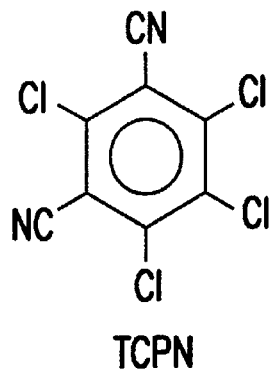
Figure 1B:
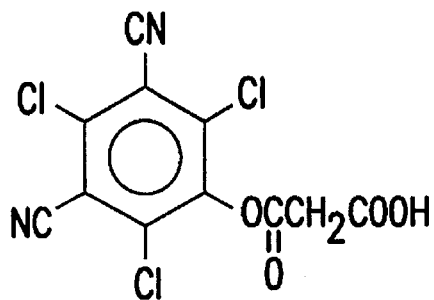
Figure 1C:
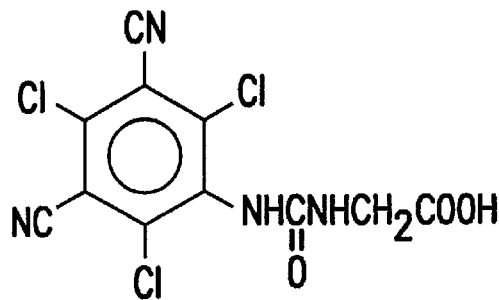
Figure 1D:
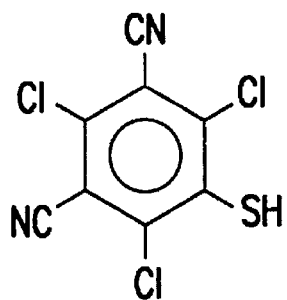
Figure 1E:
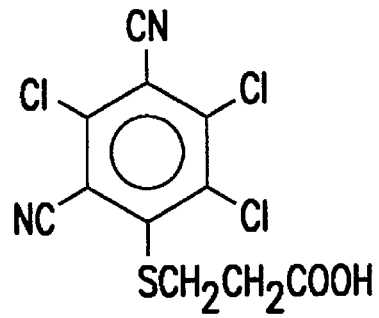
Figure 2:
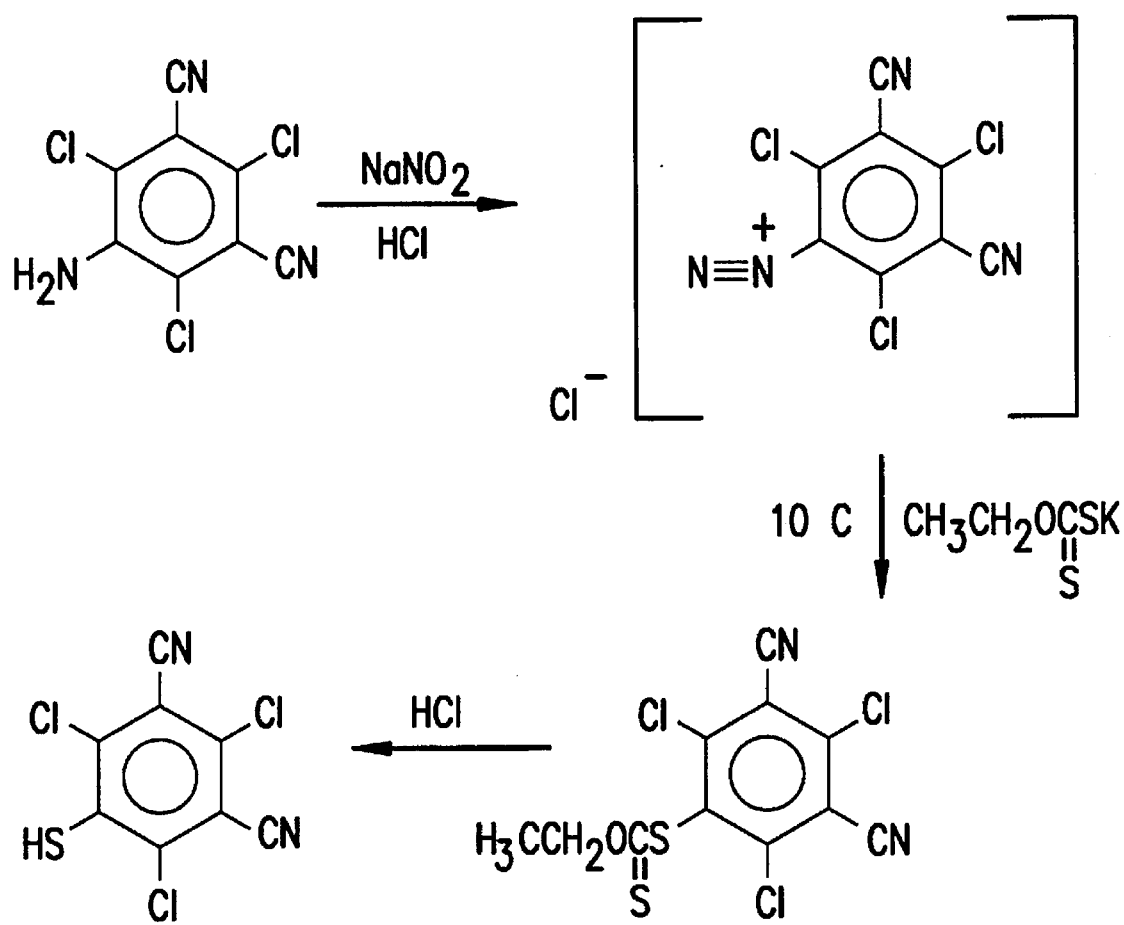
FIG. 2 shows the synthetic pathway for producing a mercapto derivative of TCPN at the 5-position.
Figure 3:
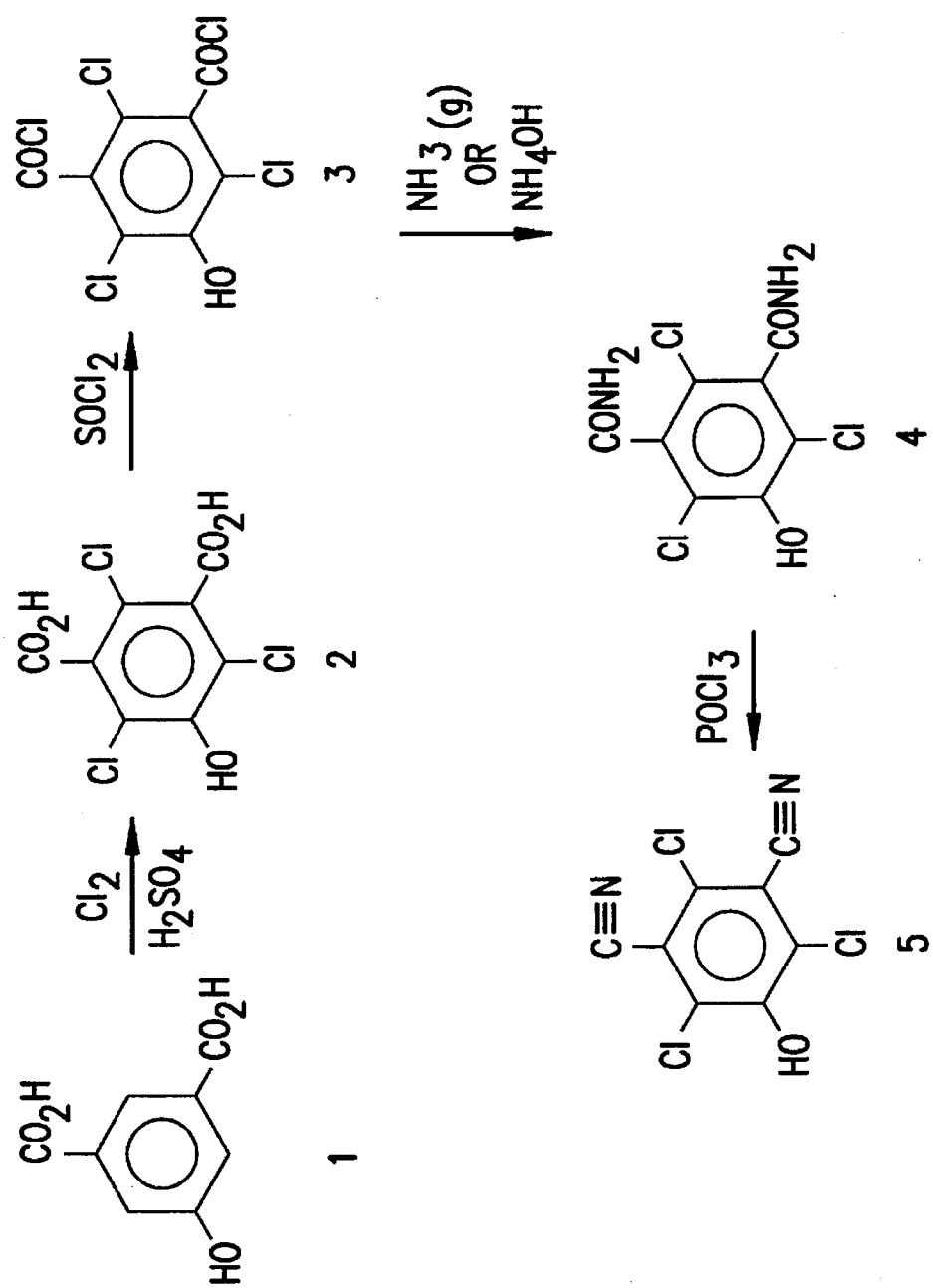
FIG. 3 shows the synthetic pathway for producing 5-hydroxy-TCPN.

Synthetic conditions for the preparation of 5-hydroxy-TCPN were developed and a supply of this compound was synthesized, according to the reaction scheme shown in FIG. 3.

Figure 4:
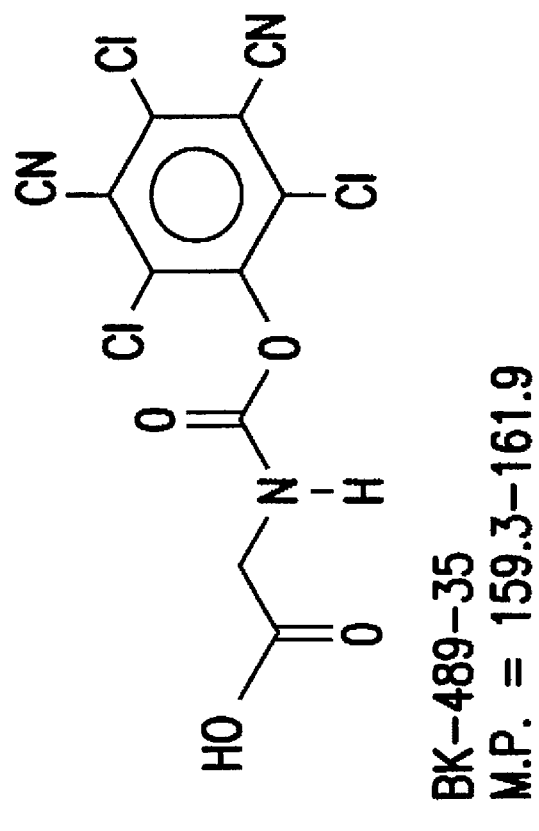
FIG. 4 shows the synthetic pathway for producing the TCPN derivative designated BK-489-35 from 5-hydroxy-TCPN.
Figure 4:
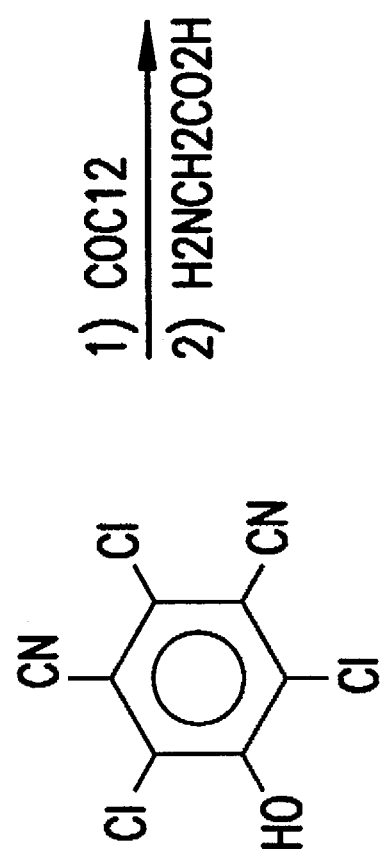
Figure 5:
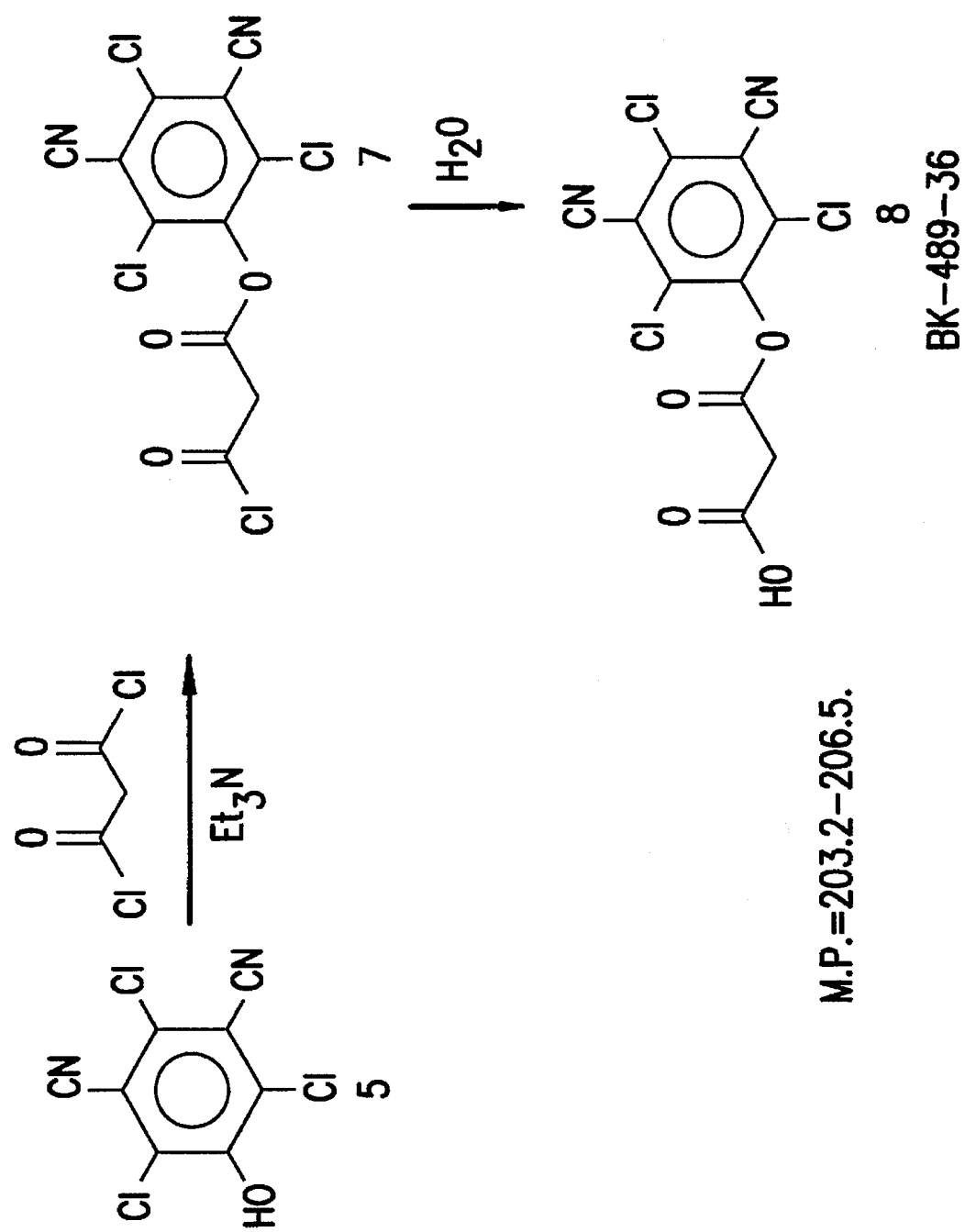
FIG. 5 shows the synthetic pathway for producing the TCPN derivative designated BK-489-36 from 5-hydroxy-TCPN.

The 5-hydroxy-TCPN was then used to prepare two derivatives with carboxylic acid functions for coupling to proteins. The first, BK-489-35, involved phosgenation followed by reaction with glycine, as shown in FIG. 4. BK-489-36 was prepared by the reaction of 5-hydroxy-TCPN with malonyl dichloride, as described in FIG. 5.

Figure 6:
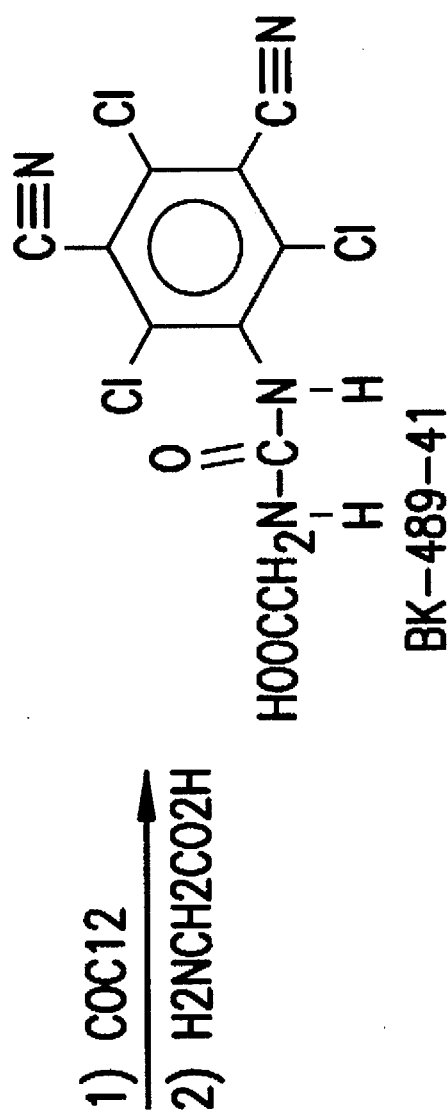
FIG. 6 shows the synthetic pathway for producing a carboxylic acid functional TCPN derivative designated BK-489-41 from 5-amino-TCPN.
Figure 6:
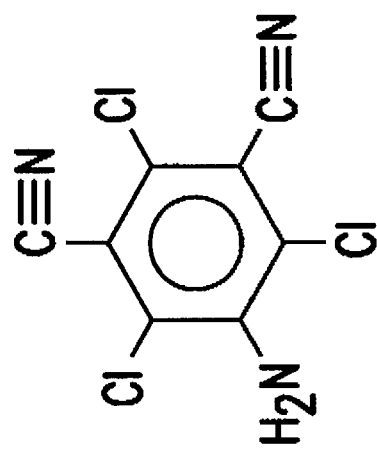

A sample of 5-amino-TCPN was obtained from Ricerca and used to prepare a carboxylic acid functional hapten, designated BK-489-41, using a procedure analogous to that used to prepare BK-489-35, as described in FIG. 6.

Conjugates were prepared using a variety of different haptens and conjugation techniques. In each case, reactions were analyzed by gel filtration HPLC with photodiode array UV-visible monitoring to determine degree of protein crosslinking and amount of free hapten remaining in solution. Upon completion of the coupling reaction, free hapten and solvents were removed by gel filtration chromatography followed by exhaustive dialysis. Whenever possible, the loading of hapten in the protein conjugate was estimated using UV-visible spectrophotometry.

7. EXAMPLE: 5-HYDROXY-TCPN CONJUGATES

The 5-hydroxy-TCPN derivatives were synthesized as described above in Section 6.

BK-489-35 was found to have extremely low solubility in water or polar organic solvents, so only very low concentrations could be dissolved in protein solution for conjugation, resulting in low loading of the hapten on the protein. This conjugate was not used for immunization.

BK-489-36 was found to have higher solubility in polar solvent (4.5 mg/ml DMF), so a bovine serum albumin (BSA) conjugate was prepared using a 15.8 fold molar excess of hapten in the reaction mixture. A mixed anhydride procedure was employed in which the hapten was first reacted in dry DMF with an equimolar amount of isobutyl-chloroformate in the presence of triethylamine, and the resulting mixed anhydride was then reacted with an aqueous solution of BSA. This resulted in a loading of 2.2 moles hapten per mole BSA in the final conjugate, as estimated by UV-visible absorbance at 340 nm and 280 nm. This conjugate was used to immunize sheep and mice.

A keyhole limpet hemocyanin (KLH) conjugate was also prepared by this method. KLH is a very high molecular weight protein which tends to elicit a strong immune response in animals. KLH is somewhat more difficult to handle than BSA due to a lower water solubility, less defined molecular weight, and aggregation at low pH, so conjugation is usually attempted with BSA first and the most promising conjugations repeated with KLH. In this case, the conditions of the BSA conjugation were repeated with the exception that the level of hapten was increased two fold. The loading achieved was estimated to be comparable to that for the BSA conjugate. This conjugate was also used to immunize sheep and mice.

A chicken albumin conjugate (Cl-O-111) was prepared using the same conditions as the KLH conjugation, with loading comparable to the BSA and KLH conjugates. This was coated on multiwell plates for use in screening antisera of sheep immunized with TCPN conjugates. The use of a screening conjugate utilizing a carrier protein different from the immunogen carrier protein avoids the undesired detection of antibodies to the immunogen protein rather than the hapten in the screening assay. Thus, BSA and KLH are preferably used as immunogen proteins and chicken albumin is used as screening conjugate protein.

8. EXAMPLE: 5-AMINO-TCPN CONJUGATES

The structure and preparation of BK-489-41 was described above and in FIG. 6. BK-489-41 was found to have high solubility in water and polar organic solvents. A mixed anhydride reaction was performed similar to that used for the 5-hydroxy derivatives, with the exception that a much higher molar excess (123-fold) of hapten could be used. The resulting conjugate has not been characterized for loading due to the fact that unlike the 5-hydroxy derivatives, this hapten does not have a distinct chromophore to differentiate it from the protein.

9. EXAMPLE: MERCAPTO-TCPN CONJUGATES

As an additional approach to conjugate development, conjugates of haptens with a sulfur replacing the chlorine at the 4-position were prepared. It is important that the antibodies of the present invention have low crossreactivity for 4-hydroxy-TCPN. Substitution at the 4-position would not ordinarily be a practical way of achieving this. Because sulfur is similar in size and electronic configuration to chlorine, antibodies induced by 4-mercapto derivatives would be expected to recognize unmodified TCPN more readily than the 4-hydroxy-TCPN.

Several approaches to coupling through the 4-mercapto position were used.

9.1. Conjugates using SPDP

N-Succinimidyl-3-(2-pyridyldithio)propionate (SPDP) was used to attach the hapten through a dithio bond and a three carbon spacer to the ε-amino groups of lysine in the protein.

The 4-mercapto hapten was conjugated to BSA using SPDP. BSA was incubated with a 40-fold excess of SPDP for 30 minutes. Unreacted SPDP was then removed by gel filtration chromatography, and the resulting activated BSA was found to have 14 SPDP units substituted per mole BSA by dithiothreitol reduction. The activated BSA was then incubated with a 48-fold molar excess of 4-mercapto-TCPN acid in DMF. The resulting conjugate was estimated to have 2.1 moles of hapten per mole of BSA. However, this may underestimate loading, since the absorbance maximum of the hapten appeared to shift upon conjugation. This conjugate was used to immunize rabbits.

9.2. Conjugates Using LC-SPDP or SMPT

A long chain SPDP analogue, succinimidyl 6-[3-(2-pyridyldithio) propionamido] hexanoate (LC-SPDP) and an aromatic analogue 4-succinimidyloxycarbonyl-α-methyl-α-(2-pyridyldithio)-toluene (SMPT) were also used to prepare conjugates with different bridge structures in an effort to increase stability in vivo and provide conjugates with unique immunogenic properties.

SMPT was used to prepare a BSA conjugate using the same conditions as the SPDP conjugate. This reagent gives a linkage that is more rigid and more stable in vivo than that resulting from SPDP conjugation. This conjugate was used to immunize rabbits.

LC-SPDP was also used to prepare a BSA conjugate using the same conditions as the SPDP conjugate. This reagent gives a linkage that is longer than that resulting from SPDP conjugation. This conjugate was used to immunize rabbits.

9.3. Conjugates with Thiolated Protein

In addition, BSA was thiolated using 2-iminothiolane (Traut's reagent) and incubated with the parent TCPN in an attempt to displace the chlorine in the 4-position by the protein-bound thiol, as described in Section 5, above.

9.4. Conjugates with Thiopropionic Acid Derivative

A thiopropionic acid derivative at the 4-position was prepared for coupling through the carboxylic acid.

9.5. Conjugates of TCPN Acid/Amide Metabolite

An acid/amide TCPN metabolite was conjugated directly to BSA (and to poly-L-lysine) using a mixed anhydride reaction as described for the 5-hydroxy derivatives. Reactions were performed at 115- and 57-fold molar excess of hapten. The 115-fold excess gave an insoluble conjugate, so the 57-fold excess conjugate was used for immunization of mice and sheep. Loading of hapten could not be determined for this conjugate by UV-visible absorbance due to the lack of a distinctive hapten chromophore.

A ovalbumin conjugate was prepared using the same procedure as that used for the 57-fold excess BSA conjugate. Multiwell plates were coated with this for screening of antisera from animals immunized with metabolite immunogens.

10. EXAMPLE: PRODUCTION OF THE TCPN ACID/AMIDE METABOLITE 46851-GLYCINE AND CONJUGATES THEREOF

Figure 7:
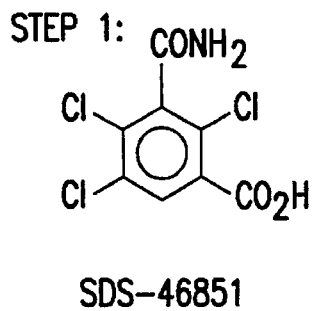
FIG. 7 shows the synthetic pathway for producing the acid/amide TCPN metabolite hapten, designated 46851-glycine (compound 7) from the acid/amide derivative 46851.
Figure 7:
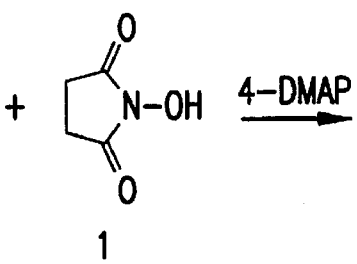
Figure 7:
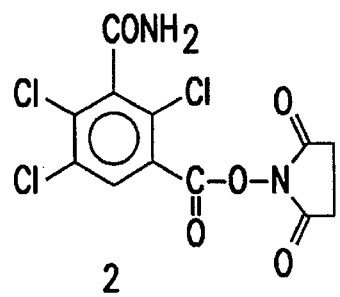
Figure 7:
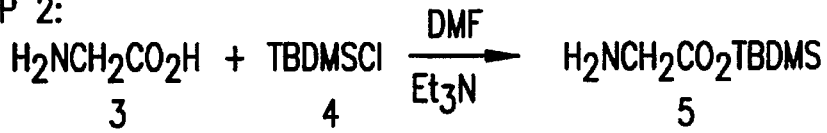
Figure 7:
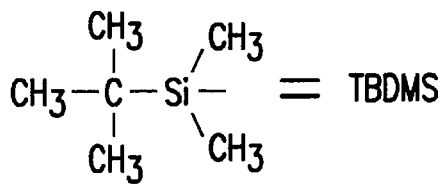
Figure 7:
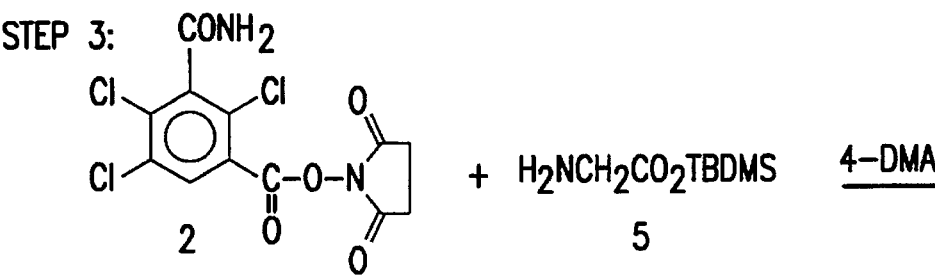
Figure 7:
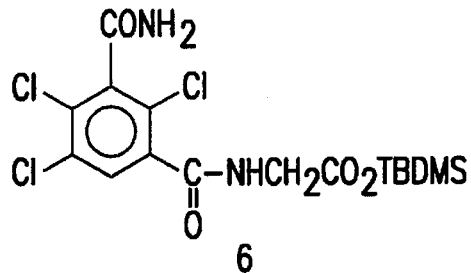
Figure 7:
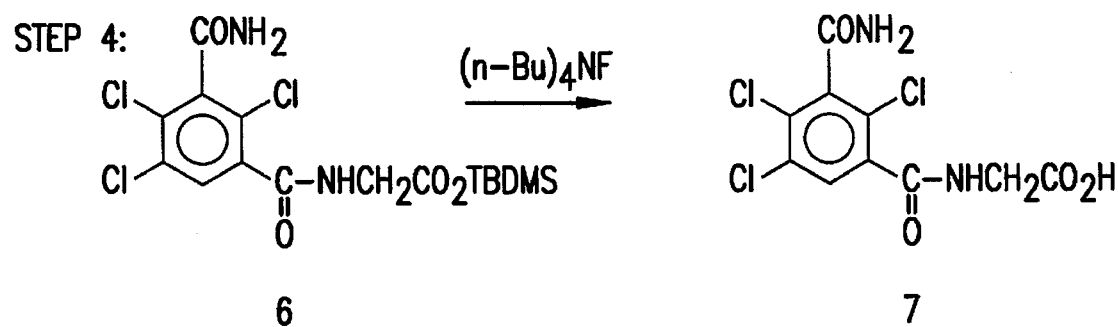
Figure 8B:
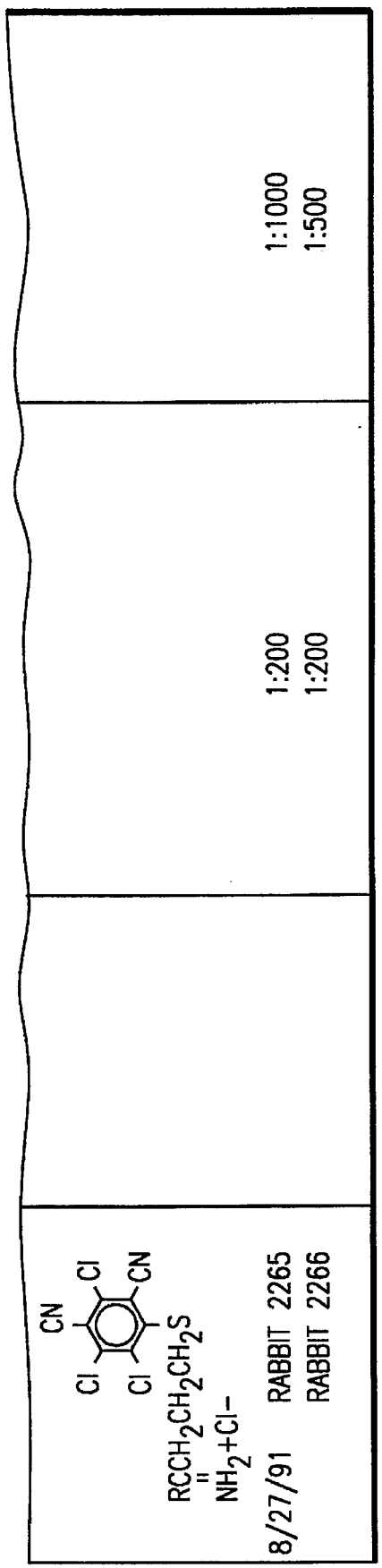
Figure 10:
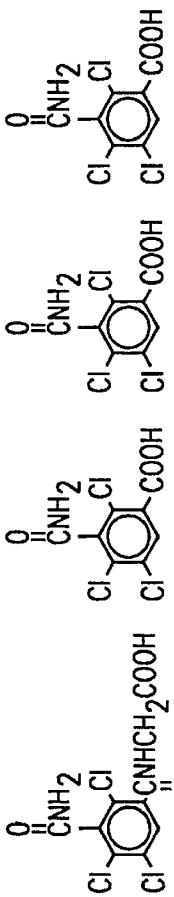
FIG. 10 shows antibody titers of sera from sheep immunized with one of two 46851 immunogenic conjugates tested in EIA on various 46851-based screening conjugates.

The acid/amide TCPN metabolite, designated 46851 (structure shown in FIG. 7), was used to synthesize the hapten 46851-glycine in four steps as described in FIG. 7, below. In the first step, the N-hydroxysuccinimidyl ester of SDS-46851 was generated (compound 2). The second step involved selective protection of the carboxylic acid moiety in glycine with a stoichiometric amount of t-butyl dimethylsilyl chloride to form the silyl ester (compound 5). The active ester 2 and the silyl ester 5 were dissolved in acetonitrile containing a catalytic amount of 4-dimethylaminopyridine to form the amide 6 in Step 3. Finally, the protecting group was removed by treatment with tetrabutyl ammonium fluoride to give the desired 46851-glycine (compound 7). 46851-glycine was isolated by acid-base neutralization, and the product was recrystallized once from dimethylformamide followed by a second recrystallization from methylene chloride. The off-white solid obtained gave proton NMR and IR consistent with the assigned structure. Because this compound retains little of the distinctive structure of TCPN, it would be expected to have little reactivity in an immunoassay which is highly specific for TCPN. A separate immunoassay was therefore developed for this compound.

Since unmodified 46851 contains a carboxylic acid group, it is possible to conjugate it directly to protein or to a spacer group. Antibodies raised to this immunogen would be expected to have a high crossreactivity for a diamide metabolite, but it is assumed that this would have little importance due to low prevalence of such metabolites. Thus, a mixed anhydride reaction was used to couple 46851 to BSA.

For the 46851-glycine hapten, a BSA immunogen conjugate was synthesized by coupling reaction with an active ester reaction as described above. An active ester conjugate was prepared with a 100-fold excess of hapten in the reaction mixture.

11. EXAMPLE: IMMUNIZATION OF SHEEP, RABBITS AND MICE

Polyclonal antibodies are preferably produced in large animals such as sheep in order to collect larger volumes of serum. However, polyclonal antibodies made in any animal species may be used in accordance with the present invention.

11.1. Sheep Immunization

The following schedule was used for immunization of sheep that received immunogens developed from 5-hydroxy-TCPN.

| DAY | INJECTION OR BLEED |
|---|---|
| 0 | 3.0 ml priming immunization |
| 30 | 2.0 ml booster immunization |
| 38 | test bleed |

11.2. Rabbit Immunization

The following schedule was used for immunization of rabbits.

| DAY | INJECTION OR BLEED |
|---|---|
| 0 | 0.5 ml priming immunization |
| 14 | 0.5 ml booster immunization |

-continued

| DAY | INJECTION OR BLEED |
|---|---|
| 21 | test bleed |
| 28 | 0.5 ml booster immunization |
| 35 | test bleed |

11.3. Mouse Immunization

The following schedule was used for immunization of mice used to generate the mAb producing cell line.

| DAY | INJECTION OR BLEED |
|---|---|
| 0 | 150 μg priming immunization, i.p. |
| 14 | 150 μg booster immunization, i.p. |
| 28 | 150 μg booster immunization, i.v. |
| 32 | harvest cells for fusion |

11.4. Polyclonal Antibody Responses in Rabbits and Sheep

FIGS. 8–10 show the antibody titers determined in EIA of sera obtained from rabbits (FIG. 8) and sheep (FIGS. 9 and 10) immunized with immunogen conjugates of TCPN which had been produced by conjugating various TCPN derivatives to an immunogenic carrier (BSA). The sera were tested against an array of screening conjugates produced using various TCPN derivatives. The structure and designation of the TCPN derivatives used to make the immunogen conjugates and screening conjugates are shown in the body of the Figures.

12. EXAMPLE: PRODUCTION OF SCREENING CONJUGATES

Chicken albumin conjugates were prepared using haptens produced as described above for preparation of immunogen conjugates.

Conjugates substituted with sulfur at position 4 of TCPN were found to give the best binding to antibodies in screening assays.

12.1. 4-Mercapto-TCPN-LC-SPDP Chicken Albumin Conjugate

A conjugate was prepared as in Section 9.2 above, with the exception that chicken albumin was used as the carrier protein.

12.2. AHT Chicken Albumin Conjugate

A new screening conjugate (Cl-O-AHT) was prepared using a method similar to that developed for preparation of the immunogen conjugate described in Section 9.3, above based on thiolation of the protein carrier and incubation with TCPN.

Chicken albumin was thiolated using N-acetylhomocysteine thiolactone (AHT) and then incubated with TCPN to cause binding to the thiol. Since the immunogen conjugate had been thiolated using 2-iminothiolane, the AHT spacer portion of the screening conjugate should not be recognized by an antibody specific for the linker.

Antibody titers measured with the Cl-O-AHT screening conjugate were up to 100-fold higher than titers measured using the LC-SPDP conjugate.

13. EXAMPLE: PRODUCTION OF ANTIBODY TO ACID/AMIDE METABOLITE OF TCPN

Spleen cells from a mouse injected with CM-B-144 (acid/amide metabolite conjugated to BSA-ethylenediamine), as described above, were fused with myeloma cells to produce hybridomas. Sixty cell lines were isolated from this fusion for further evaluation. Fourteen cell lines continued to show activity on CM-B-150 (46481-BSA) screening plates upon scale up. These fourteen lines were tested for isotype to identify the antibody subclass (Table I). Of the 14 cell lines, two lines were secreting IgG1 antibody, five lines were secreting IgM antibody, and seven lines stopped secreting.

TABLE I

Isotyping Results from the CM-B-144 Fusion Cell Lines

| Isotype | Cell Lines |
| --- | --- |
| IgG1 | 6C10, 8F3 |
| IgM | 2D2, 1D11, 1E11, 3B9, 8C8 |
| No Ig | 2B2, 2C2, 1D10, 1b11, 5B7 |
|  | 1E3, 5E3 |

Since IgG1 antibodies are preferred for immunoassays, the two IgG1-producing lines were scaled up and the remaining lines were frozen for future evaluation.

The 6C10 and 8F3 antibodies were tested for sensitivity to the acid/amide metabolite 46851. Each line yielded 50% inhibition at 20,000 ppb. Both lines were then subcloned in an attempt to improve the sensitivity. The multiclone was scaled-up for antibody purification.

Crude 6C10 supernatant (30 ml) was purified by Protein A affinity chromatography to isolate the IgG molecules. Multiwell plates were coated with 5, 10, 20 and 40 µg/ml of the antibody in carbonate/bicarbonate buffer (pH 9.6). The peroxidase conjugate, CM-H-150, was used to test the plates in a direct format at concentrations ranging from 5–160 µg/ml in standard conjugate storage buffer and in high salt conjugate storage buffer C using the "high sensitivity" format.

Standard conjugate storage buffer gave the best results; the "high sensitivity" format using buffer C gave poor color development, so inhibition was not tested. Sensitivity was tested using 160 µg/ml CM-B-150 in standard conjugate storage buffer and plates coated with 40 µg/ml antibody. Inhibition of 50% was seen in the presence of 20,000 ppb of the 46851 acid/amide metabolite, which is equivalent to the sensitivity of the indirect assay.

A second set of plates was coated using the following buffers: (1) 100 mM glycine with 0, 150 mM, or 500 mM NaCl; or (2) 20 mM PBS with 0, 150 mM or 500 mM NaCl.

The binding of antibody to the plates was evaluated using the CM-B-150 conjugate in a direct assay. Incubation time was increased to 20 minutes to enhance sensitivity. Very little activity was seen in this format with either the glycine or the PBS buffer system. The carbonate/bicarbonate plate coating buffer appeared to give the best sensitivity in the direct format.

The uncloned ("multiclone") hybridoma, 8F3, was scaled up for antibody purification.

Neither of the purified 6C10 nor 8F3 mAbs appeared to be any more sensitive than the crude supernatant; two consecutive subclonings revealed sensitivity that was the same as the multiclone.

Evaluation of sera obtained from mice immunized with the CM-B-150 and CM-B-144 conjugates are described in Table II, below.

TABLE II

Antibody Responses of Mice Immunized with Acid/Amide Metabolite

| Antigen | Date | Titer[1] | $IC_{50}$ (ppb)[2] |
| --- | --- | --- | --- |
| CM-B-150 | 3/25 | 1:90,000(purple) | 4500 |
|  |  | 1:60,000(white) | 11000 |
|  |  | 1:60,000(blue) | 11000 |
|  | 4/09 | 1:200,000(purple) | 1075 |
|  |  | 1:70,000(white) | 1000 |
|  |  | 1:70,000(blue) | 11000 |
|  | 4/23 | 1:90,000(purple) | 1500 |
|  |  | 1:90,000(white) | 6000 |
|  |  | 1:50,000(blue) | 9000 |
|  | 5/07 | 1:80,000(purple) | 1000 |
|  |  | 1:75,000(white) | 5000 |
|  |  | 1:50,000(blue) | 10000 |
| CM-B-144 |  |  |  |
| Grp 1 | 3/25 | 1:90,000 | 5000 |
|  | 4/09 | 1:150,000 | 3000 |
| Grp 2 | 3/5 | 1:90,000(purple) | 2000 @ 80% max. abs. |
|  |  | 1:90,000(white) | 2000 @ 74% max. abs. |
|  | 3/19 | 1:90,000(purple) | 11000 |
|  |  | 1:90,000(white) | 9500 |
|  | 4/09 | 1:80,000(purple) | 1000 |
|  |  | 1:80,000(white) | 6000 |
|  | 4/23 | 1:50,000(purple) | 9000 |
|  | 4/24 | 1:70,000(white) | 5000 |
|  | 5/07 | 1:25,000(purple) | 1250 |
|  |  | 1:30,000(white) | 7000 |

[1]Titers represent the dilution of antiserum required to give an $A_{650}$ value of 1.50 in the indirect screening assay on the respective plates.
[2]$IC_{50}$ is the concentration (in parts per billion, ppb) of free acid/amide metabolite required to give 50% inhibition in the indirect screening assay with the antiserum at it's respective titer concentration.

An additional group of mice were immunized with Cl-B-122, the conjugate made by directly thiolated BSA and reacting with TCPN, resulting in a protein substituted with the mercapto derivative of TCPN. After two i.p. immunizations, the mice received one i.v. immunization, as described above, and 4 days later, spleen cells were harvested and fused with SP2 myeloma cells.

Supernatants from resulting hybridomas were screened using multiwell plates coated with Cl-O-AHT at 1 µg/ml. Antibody isotypes were also determined. Supernatants with activity above 0.6 absorbance units were further evaluated for their ability to inhibit binding of the parent molecule. Results of twelve cell lines are shown in Table III, below.

TABLE III

Evaluation of Supernatants of Anti-TCPN Hybridomas (Multiclones)

| Cell Line | Isotype | Absorbance | $IC_{50}$ |
| --- | --- | --- | --- |
| 6F9 | IgG1 | 1.365 | 50 ppb |
| 1A5 | IgG1, IgG2a IgM, κ | 0.925 | no inhibition |
| 2D9 | IgG1 | 0.073 |  |
| 3F11 | IgM, κ | over | no inhibition |
| 4B9 | IgM, κ | over | no inhibition |
| 4D7 | IgG1, κ | 0.376 |  |
| 5D3 | IgM, κ | over | no inhibition |
| 5E5 |  | 0.041 |  |
| 7D5 |  | 0.240 |  |
| 8F3 | IgG2a, IgM, κ | 0.133 |  |

TABLE III-continued

Evaluation of Supernatants of
Anti-TCPN Hybridomas (Multiclones)

| Cell Line | Isotype | Absorbance | IC$_{50}$ |
|---|---|---|---|
| 3F6 | IgM, κ | 2.636 | no inhibition |
| 1B2 | IgM, κ | 0.042 | |

Cell line Cl-B-122-6F9 (designated 6F9) showed strong activity when tested in indirect ELISA and 50% inhibition at the 50 ppb level. The twelve lines described in Table III were subcloned to assure purity and stability. The 6F9 cell line was scaled up for assay development and the remaining lines were cryopreserved.

14. EXAMPLE: FURTHER ASSAY DEVELOPMENT

14.1. Optimization of Coating Level of Cl-O-AHT Screening Conjugate

A comparison was performed on antibody binding to plates coated with the Cl-O-AHT conjugate and the 4-mercapto-TCPN-LC-SPDP-chicken albumin conjugate (Cl-O-157) described in Section 12, above. Sensitivity of plates coated with Cl-O-AHT at concentrations of 20 µg/ml was below that of plates coated with 20 µg/ml of the 4-mercapto conjugate. However, assay sensitivity improved as the coating concentration of Cl-O-AHT decreased, so that at 1 µg/ml of Cl-O-AHT, the assay was more sensitive than the indirect assay using a 4-mercapto-LC-SPDP conjugate Cl-O-157.

At coating concentrations below 1 µg/ml, no further improvement in assay sensitivity was observed. Thus, 1 µg/ml was selected as the preferred concentration for immunoassay development.

14.2. High Sensitivity Assay Format

Antiserum from sheep 1116, which had been immunized with Cl-B-122, was evaluated on plates coated with Cl-O-157 in the "high sensitivity" format (high salt buffer to dilute the antiserum and a higher sample volume). In prior studies, this assay format improved the sensitivity of the indirect assays of rabbit antisera.

The results of assays performed using the high sensitivity format with antisera from sheep 1159 and sheep 1116, and plates coated with 1 µg/ml Cl-O-AHT indicate that the sensitivity was improved under these conditions. Antiserum from sheep 1116 yielded a standard curve showing 20% inhibition at 0.5 ppb, 50% inhibition at 5 ppb, and 80% inhibition at 50 ppb. Antiserum from sheep 1159 resulted in a broader standard curve, with 50% inhibition obtained at 10 ppb.

15. EXAMPLE: ENZYME IMMUNOASSAY OF TCPN, CROSSREACTIVITY, AND DETECTION OF TCPN IN SPIKED WATER SAMPLES

The following immunoassay protocol was followed

1. Microplates were prepared by binding screening conjugate Cl-O-AHT to the polystyrene surface.
2. An appropriately diluted sample (200 µl) and the anti-TCPN antibody conjugated to horse radish peroxidase (50 µl) were added and incubated for 10 minutes.
3. The wells were rinsed, and 200 µl of substrate, tetramethyl benzidine (TMB), was added to the wells.
4. The plates were incubated for a further 10 minutes and 50 µl of stop solution (1.5% NaF) was added.
5. The color reaction was read by measuring absorbance at 650 nm.

Standard curves were generated for TCPN (Chlorothalanil) using a polyclonal antibody and mAb 6F9. Results are shown in FIGS. 11A and 11B.

The cross reactivity of various TCPN derivatives and other benzene ring-based haptens were assessed using the above antibody preparations. Table IV, below, shows the reactivity profiles of the mAb and polyclonal antibody-based EIAs. FIG. 12 shows the cross-reactivity response curves with the mAb.

TABLE IV

REACTIVITY PROFILE OF TCPN EIA

| | Monoclonal Antibody | | Polyclonal Antibody | |
|---|---|---|---|---|
| Analyte | IC50 (ppb) | $^1$% Cross Reactivity | IC50 (ppb) | % Cross Reactivity |
| TCPN | 2.2 | 100 | 5.0 | 100 |
| PCBN* | 30 | 7.3 | 60 | 8.3 |
| 4-hydroxyTCPN(4-hydroxy-2,5,6-trichloroisophthalonitrile) | 8.0 | 28 | 1010 | 0.5 |
| acid/amide TCPN(3-carbamyl-2,4,5-trichlorobenzoic acid) | >10$^4$ | <0.01 | >10$^4$ | <0.01 |
| 4-aminoTCPN(4-amino-2,5,6-trichloroisophthalonitrile) | 2.4 | 92 | 43 | 12 |
| 4-mercaptoTCPN(4-mercapto-2,5,6-trichloroisophthalonitrile) | 4.8 | 46 | 10 | 60 |
| 5-hydroxyTCPN(5-hydroxy-2,4,6-trichloroisophthalonitrile) | 7.0 | 31 | 800 | 0.6 |
| 5-amino-TCPN(5-amino-2,4,6-trichloroisophthalonitrile) | 1.9 | 116 | 43 | 12 |
| amide TCPN(2,4,5,6-tetrachloro-3-cyanobenzamide) | 800 | 2.8 | 700 | 0.7 |
| HCB** | >10$^4$ | <0.01 | >10$^4$ | <0.01 |
| Alachlor ® | >10$^4$ | <0.01 | >10$^4$ | <0.01 |
| Metolachlor ® | >10$^4$ | <0.01 | >10$^4$ | <0.01 |
| Atrazine | >10$^4$ | <0.01 | >10$^4$ | <0.01 |
| Trifluralin ® | >10$^4$ | <0.01 | >10$^4$ | <0.01 |
| Benomyl ® | >10$^4$ | <0.01 | >10$^4$ | <0.01 |
| MBC*** | >10$^4$ | <0.01 | >10$^4$ | <0.01 |

*PCBN: pentachlorobenzonitrile
**HCB: hexachlorobenzene
***MBC: carbendazim (metabolite of Benomyl ® )7
$^1$% Cross Reactivity = IC50 of TCPB/IC50 of test compound × 100

The validity of the above immunoassays was tested by measuring TCPN in samples of tap water, pond water, or river water which had been spiked with TCPN in the range of 0.01 to 62.5 ppb. Eighteen samples of each type of water were tested with the polyclonal antibody-enzyme conjugate and the mAb-enzyme conjugate, as well as by gas chromatography. The results are shown in FIGS. 13–15.

In the spiked tap water samples, correlation between immunoassay and GC results were good, although the immunoassay tended to overestimate low concentrations and underestimate high concentrations relative to GC. With pond water, similar results were obtained. For TCPN-spiked river water, the correlation was good between GC and immunoassay, although unspiked water gave a "false positive" result in immunoassay (and was not tested in GC). River water spiked with higher concentrations of TCPN have lower results by immunoassay.

In general, the above results point to the validity of the immunoassay systems of the present invention for detection of TCPN in aqueous fluids.

Further assay validation was conducted by examining the recovery of TCPN which had been added to tomato samples. Untreated tomatoes were blended, and 10 g portions were spiked with TCPN. The spiked puree was extracted with acid acetone, diluted 1:50 with water an tested in the EIA using a polyclonal antibody-enzyme. The results are shown in Table V, below.

TABLE V

Concentration of TCPN (in ppm) in Spiked Tomato Extracted with Acid Acetone

| Spike Level | Amount Recovered | % Recovery |
|---|---|---|
| 0.10 | 0.12 | 120% |
| 0.49 | 0.51 | 104% |
| 0.98 | 1.01 | 103% |
| 4.9 | 5.6 | 115% |
| 9.7 | 10.3 | 106% |
| 19.6 | 23.6 | 121% |

The above results indicate that recovery of TCPN from a tomato sample and its detection by immunoassay is excellent.

16. EXAMPLE: DETECTION OF TCPN IN SPRAYED TOMATOES

Thirty tomatoes were collected from plants at time of sixth application of TCPN. One group of tomatoes was collected immediately prior to spraying so that they were analyzed one week after the fifth spraying. A second group was collected immediately after the sixth spraying. A control group comprised untreated tomatoes.

Tomatoes were macerated in a blender and the macerated fruit was extracted with acid acetone. The resulting slurry was filtered and washed with acid acetone. The extract was diluted 1:50 in water for analysis.

The amount of TCPN (in ppb) was measured by gas chromatography (GC) and with an immunoassay as described above based on an anti-TCPN polyclonal antibody. Table VI shows the measurement of TCPN by polyclonal EIA (and GC) in 30 tomato extracts.

TABLE VI

Measurement of TCPN by Gas Chromatograph (GC) and Polyclonal Antibody Based Enzyme Immunoassay (EIA)

| Group | GC | Polyclonal EIA |
|---|---|---|
| Controls | 0.00 | 0.04 |
| | 0.01 | 0.05 |
| | 0.00 | 0.04 |
| | 0.00 | 0.03 |
| | 0.00 | 0.12 |
| | 0.00 | 0.03 |
| | 0.00 | 0.01 |
| | 0.00 | 0.00 |
| | 0.00 | 0.00 |
| | 0.01 | 0.04 |
| One Week Post Fifth Spray | 0.58 | 0.82 |
| | 0.56 | 0.69 |
| | 0.23 | 0.67 |
| | 1.08 | 2.28 |
| | 0.02 | 1.00 |
| | 0.56 | 0.57 |
| | 1.42 | 2.23 |
| | 1.72 | 1.77 |
| | 0.65 | 0.89 |
| | 0.34 | 0.19 |
| | 0.97 | 1.10 |
| Immediately Post Sixth Spray | 0.69 | 1.08 |
| | 1.05 | 1.24 |
| | 1.01 | 1.02 |
| | 0.04 | 3.42 |
| | 0.30 | 4.50 |
| | 0.57 | 0.54 |
| | 1.72 | 1.77 |
| | 0.37 | 0.63 |
| | 0.43 | 0.43 |
| | 0.62 | 0.49 |

The correlation ($r^2$) between the concentrations of TCPN determined by GC vs. and EIA was 0.637 (see FIG. 16).

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. An antibody useful in an immunoassay to detect or measure tetrachloroisophthalonitrile (TCPN) or a TCPN metabolite in a sample, wherein
    i) said TCPN metabolite is 4-hydroxy-2,5,6-trichloroisophthalonitrile, or 3-carbamyl-2,4,5-trichlorobenzoic acid; and
    ii) said antibody specifically binds TCPN or said TCPN metabolite.

2. The antibody of claim 1, which specifically binds tetrachloroisophthalonitrile, 4-hydroxy-2,5,6- trichloroisophthalonitrile, and 3-carbamyl-2,4,5-trichlorobenzoic acid.

3. The antibody of claim 1, which is a polyclonal antibody, and which specifically binds tetrachloroisophthalonitrile and exhibits no greater than about 0.5% cross-reactivity with 4-hydroxy-2,5,6-trichloroisophthalonitrile in said immunoassay.

4. The antibody of claim 1, which is a polyclonal antibody, and which specifically binds tetrachloroisophthalonitrile, and exhibits less than about 0.01% cross-reactivity with 3-carbamyl-2,4,5-trichlorobenzoic acid in said immunoassay.

5. The antibody of claim 1, which specifically binds tetrachloroisophthalonitrile.

6. The antibody of claim 1, which is a polyclonal antibody and is capable of detecting tetrachloroisophthalonitrile at about 5.0 parts per billion of said sample in said immunoassay.

7. The antibody of claim 1, which specifically binds 4-hydroxy-2,5,6-trichloroisophthalonitrile.

8. The antibody of claim 1, which specifically binds 3-carbamyl-2,4,5-trichlorobenzoic acid.

9. A monoclonal antibody produced by the 6F9 hybridoma cell line having ATCC accession number HB 11395.

10. Hybridoma cell line 6F9 having ATCC accession number HB 11395.

11. An antibody useful in an immunoassay to detect or measure a TCPN derivative in a sample, wherein
   i) said TCPN derivative is a compound selected from the group consisting of 4-amino-2,5,6-trichloroisophthalonitrile, 4-mercapto-2,5,6-trichloroisophthalonitrile, 5-hydroxy-2,4,6-trichloroisophthalonitrile, and 5-amino-2,4,6-trichloroisophthalonitrile; and
   ii) said antibody specifically binds the TCPN derivative.

12. The antibody of claim 11, which specifically binds 4-amino-2,5,6-trichloroisophthalonitrile, 4-mercapto-2,5,6-trichloroisophthalonitrile, 5-hydroxy-2,4,6-trichloroisophthalonitrile, and 5-amino-2,4,6-trichloroisophthalonitrile.

13. An antibody according to any of claims 1–12 produced by immunizing an animal with a protein carrier conjugated with a compound selected from the group consisting of 5-hydroxy-2,4,6-trichloroisophthalonitrile, 5-amino-2,4,6-trichloroisophthalonitrile, 5-mercapto-2,4,6-trichloroisophthalonitrile, 4-mercapto-2,5,6-trichloroisophthalonitrile, 4-hydroxy-2,5,6-trichloroisophthalonitrile, tetrachloroisophthalonitrile, 3-carbamyl-2,4,5-trichlorobenzoic acid.

14. The antibody of claim 13, wherein said carrier protein is bovine serum albumin or keyhole limpet hemocyanin.

15. A method for isolating from a complex mixture a compound capable of binding to the antibody of claim 1 or 2, wherein said compound is (i) 4-hydroxy-2,5,6-trichloroisophthalonitrile, or 3-carbamyl-2,4,5-trichlorobenzoic acid, or (ii) a protein conjugated with a chemical selected from the group consisting of 5-hydroxy-2,4,6-trichloroisophthalonitrile, 5-amino-2,4,6-trichloroisophthalonitrile, 5-mercapto-2,4,6-trichloroisophthalonitrile, 4-mercapto-2,5,6-trichloroisophthalonitrile, 4-hydroxy-2,5,6-trichloroisophthalonitrile, tetrachloroisophthalonitrile, and 3-carbamyl-2,4,5-trichlorobenzoic acid, and said method comprises:
   (a) immobilizing said antibody on a solid phase support or carrier;
   (b) contacting said complex mixture with said immobilized antibody allowing said compound to bind to said antibody, and washing away any unbound material; and
   (c) eluting said bound compound, thereby isolating said compound.

16. A method for producing a hybridoma cell line that produces a monoclonal antibody that specifically binds tetrachloroisophthalonitrile (TCPN) or a TCPN metabolite, wherein said TCPN metabolite is 4-hydroxy-2,5,6-trichloroisophthalonitrile, or 3-carbamyl-2,4,5-trichlorobenzoic acid, and said method comprises:
   (a) immunizing a donor animal with a protein carrier conjugated with a compound selected from the group consisting of 5-hydroxy-2,4,6-trichloroisophthalonitrile, 5-amino-2,4,6-trichloroisophthalonitrile, 5-mercapto-2,4,6-trichloroisophthalonitrile, 4-mercapto-2,5,6-trichloroisophthalonitrile, 4-hydroxy-2,5,6-trichloroisophthalonitrile, tetrachloroisophthalonitrile, and 3-carbamyl-2,4,5-trichlorobenzoic acid;
   (b) obtaining B lymphocytes from said immunized donor animal;
   (c) fusing said B lymphocytes with cells of a fusion partner cell line to obtain hybrid cells; and
   (d) selecting hybrid cells which produce antibodies that specifically binds TCPN or a TCPN metabolite by:
      (i) culturing said hybrid cells;
      (ii) screening the medium of said cultures for the presence of an antibody which binds to TCPN or a TCPN metabolite; thereby detecting antibody producing hybrid cells; and
   (e) growing said selected hybrid cells, thereby producing said hybridoma cell line.

17. A method for producing a monoclonal antibody that specifically binds tetrachloroisophthalonitrile (TCPN) or a TCPN metabolite, wherein said TCPN metabolite is 4-hydroxy-2,5,6-trichloroisophthalonitrile, or 3-carbamyl-2,4,5-trichlorobenzoic acid, and which method comprises:
   (a) culturing a hybridoma cell line according to claim 10 under conditions which permit antibody production and secretion by said cell line; and
   (b) obtaining the culture medium containing said antibody.

18. A method for producing an antibody that specifically binds tetrachloroisophthalonitrile (TCPN), a TCPN metabolite or a TCPN derivative, which comprises
   i) immunizing an animal with a macromolecular carrier conjugated with a compound selected from the group consisting of 5-hydroxy-2,4,6-trichloroisophthalonitrile, 5-amino-2,4,6-trichloroisophthalonitrile, 5-mercapto-2,4,6-trichloroisophthalonitrile, 4-mercapto-2,5,6-trichloroisophthalonitrile, 4-hydroxy-2,5,6-trichloroisophthalonitrile, tetrachloroisophthalonitrile, and 3-carbamyl-2,4,5-trichlorobenzoic acid; and
   ii) screening the serum of the animal for an antibody that specifically binds tetrachloroisophthalonitrile (TCPN), a TCPN metabolite or a TCPN derivative;
wherein said TCPN metabolite is 4-hydroxy-2,5,6-trichloroisophthalonitrile or 3-carbamyl-2,4,5-trichlorobenzoic acid, and said TCPN derivative is a compound selected from the group consisting of 4-amino-2,5,6-trichloroisophthalonitrile, 4-mercapto-2,5,6-trichloroisophthalonitrile, 5-hydroxy-2,4,6-trichloroisophthalonitrile, and 5-amino-2,4,6-trichloroisophthalonitrile.

19. The method according to claim 18, wherein the macromolecular carrier is a protein.

* * * * *